United States Patent
Petersson et al.

(10) Patent No.: US 10,947,290 B2
(45) Date of Patent: Mar. 16, 2021

(54) METHOD OF STABILIZING A BIOACTIVE PEPTIDE AGAINST PROTEASE HYDROLYSIS

(71) Applicants: THE TRUSTEES OF THE UNIVERSITY OF PENNSYLVANIA, Philadelphia, PA (US); PRESIDENT AND FELLOWS OF HARVARD COLLEGE, Cambridge, MA (US)

(72) Inventors: E. James Petersson, Wynnewood, PA (US); Alan Saghatelian, Somerville, MA (US)

(73) Assignees: The Trustees of the University of Pennsylvania, Philadelphia, PA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 16/209,128

(22) Filed: Dec. 4, 2018

(65) Prior Publication Data
US 2019/0085044 A1 Mar. 21, 2019

Related U.S. Application Data

(63) Continuation of application No. 15/305,681, filed as application No. PCT/US2015/028008 on Apr. 28, 2015, now Pat. No. 10,189,884.

(60) Provisional application No. 61/985,045, filed on Apr. 28, 2014.

(51) Int. Cl.
| | |
|---|---|
| *A61K 38/26* | (2006.01) |
| *C07K 14/605* | (2006.01) |
| *A61K 9/00* | (2006.01) |
| *C07K 1/113* | (2006.01) |
| *A61K 38/00* | (2006.01) |

(52) U.S. Cl.
CPC .......... *C07K 14/605* (2013.01); *A61K 9/0019* (2013.01); *A61K 38/26* (2013.01); *C07K 1/1136* (2013.01); *A61K 38/00* (2013.01)

(58) Field of Classification Search
CPC .................................................. C07K 14/495
See application file for complete search history.

(56) References Cited

U.S. PATENT DOCUMENTS 6,075,121 A  6/2000  Simon et al.
8,895,694 B2  11/2014  Spetzler et al.

2006/0003934 A1  1/2006  Pan et al.
2007/0161087 A1  7/2007  Glaesner et al.
2012/0021972 A1  1/2012  Bahekar et al.

FOREIGN PATENT DOCUMENTS

WO  2006108686 A2  10/2006
WO  2013172954 A1  11/2013

OTHER PUBLICATIONS

Zhang et al., Peptides 31: 1832-1838 (2010).*
Batjargal et al., J. Pept. Sci.20: 87-91,( 2014).*
International Search Report dated Sep. 8, 2015—PCT/US2015/028008.
Bird, et al.,Hydrocarbon double-stapling remedies the proteolytic Hydrocarbon double-stapling remedies the proteolytic., 2010, Proc. Natl. Acad. Sci. 107:14093-14098.
De Menthiere, et al.,Structural requirements of the N-terminal region of GLP-1-[7-37]-NH2 for receptor interaction and cAMP production., European Journal of Medicinal Chemistry 39 (2004) 473-480.
Deacon, et al.,Dipeptidyl peptidase IV resistant analogues of glucagon-like peptide-1 which have extended metabolic stability and improved biological activity., 1998, Diabetologia 41:271-278.
Drucker, et al.,The incretin system: glucagon-like peptide-1 receptor agonists and dipeptidyl peptidase-4 inhibitors in type 2 diabetes., 2006, Lancet 368:1696-1705 (Abstract).
Goldberg, et al.,Thiomide-Based Fluorescent Protease Sensors., J. Am. Chem. Soc. 2014, 136, 2086-2093.
Heard, et al.,A general method for making peptide therapeutics resistant to serine protease degradation: application to dipeptydyl peptidase IV substrates., 2013, J. Med. Chem. 56:8339-8351.
Iltz, et al.,Exenatide: an incretin mimetic for the treatment of type 2 diabetes mellitus., 2006, Clin. Ther. 28:652-665 (Abstract).
Kreymann, et al.,Glucagon-like peptide-1 7-36: a physiological incretin in man., 1987, Lancet 330:1300-1304 (Abstract).
Sato, et al.,Therapeutic peptides: technological advances driving peptides into development., 2006, Curr. Opin. Biotechnol. 27:638-642.
Tran, et al.,Effects of thioamide substitutions on the conformation and stability of alpha- and 3(10)-helices, J Am Chem Soc. 124(18) ,May 2002 ,5222-5230.

* cited by examiner

*Primary Examiner* — Gyan Chandra
(74) *Attorney, Agent, or Firm* — Saul Ewing Arnstein & Lehr LLP; Kathryn Doyle; Domingos J. Silva

(57) ABSTRACT

The invention includes a thioamide-modified peptide, wherein the thioamide modification increases the in vivo half-life of the peptide. The invention further includes methods of treating or preventing a disease or disorder in a subject in need thereof, the method comprising administering to the subject a thioamide-modified peptide of the invention.

3 Claims, 16 Drawing Sheets

Specification includes a Sequence Listing.

| Peptide | SEQ ID NO: |
|---|---|
| GLP-1 | 1 |
| GIP | 5 |
| OXM | 6 |
| BNP | 7 |
| Exenatide | 3 |
| Liraglutide | 4 |
| M1 | 8 |
| M2 | 9 |
| M3 | 10 |

L'LKAAµ = SEQ ID NO:59

AKGL'AAFAµ = SEQ ID NO:60

AKGLAAFAµ = SEQ ID NO:61

$t_{1/2} > 24$ h

Thio GLP-1 = SEQ ID NO:2, wherein Xaa (1) is Histidine

GLP-1-A$^S_8$ = SEQ ID NO:2, wherein Xaa (1) is Histidine

| Peptide | SEQ ID NO: |
|---|---|
| Glucagon | 21 |
| GLP-1 | 1 |
| GIP | 5 |
| OXM | 6 |
| BNP | 7 |
| NPY | 23 |
| PYY | 25 |
| PP | 27 |
| RANTES (CCL5) | 29 |
| CCL2 | 31 |

| Peptide | SEQ ID NO: |
|---|---|
| GLP-1 | 1 |
| Exenatide | 3 |
| Liraglutide | 4 |
| M1 | 8 |

X = O or S

| SEQUENCES | SEQ ID NO: | Papain $t_{1/2}$ (min) | Trypsin $t_{1/2}$ (min) |
|---|---|---|---|
| μLLKAAAμ | 52 | 5 | 1 |
| μL$^S$LKAAAμ | 53 | 4 | 4 |
| μLL$^S$KAAAμ | 54 | 180 | 2 |
| μLLR$^S$AAAμ | 55 | 12 | >200 |
| μLLKA$^S$AAμ | 56 | >30 | 3 |
| μLLKAA$^S$Aμ | 57 | 4 | 2 |
| μLLKAAA$^S$μ | 58 | 5 | 2 |

GIP = SEQ ID NO:5
GIP-A$^S_4$ = SEQ ID NO:13

SEQUENCE LISTING

```
<160> NUMBER OF SEQ ID NOS: 61

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15
```

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio alanine

<400> SEQUENCE: 2

Xaa Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 38
<212> TYPE: PRT
<213> ORGANISM: Homo sapiens

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Glu Phe Ile Ala Trp Leu Val Arg Gly Arg Gly
            20                  25                  30

<210> SEQ ID NO 5
<211> LENGTH: 42
<212> TYPE: PRT
<213> ORGANISM: Homo sapiens

<400> SEQUENCE: 5

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 6
<211> LENGTH: 37
<212> TYPE: PRT
<213> ORGANISM: Homo sapiens

```
<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 7
<211> LENGTH: 32
<212> TYPE: PRT
<213> ORGANISM: Homo sapiens

<400> SEQUENCE: 7

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 8
<211> LENGTH: 30
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is dimethyl glycine
<220> FEATURE:
<221> NAME/KEY: MISC_FEATURE
<222> LOCATION: (29)..(29)
<223> OTHER INFORMATION: Xaa is dimethyl glycine

<400> SEQUENCE: 8

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 9
<211> LENGTH: 30
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is t-butyl glycine

<400> SEQUENCE: 9

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 10
<211> LENGTH: 30
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is beta, beta-dimethyl aspartic acid

<400> SEQUENCE: 10

His Ala Xaa Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg
            20                  25                  30

<210> SEQ ID NO 11
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio glycine

<400> SEQUENCE: 11

Xaa Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 12
<211> LENGTH: 31
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio alanine
<220> FEATURE:
<221> NAME/KEY: MISC_FEATURE
<222> LOCATION: (20)..(20)
<223> OTHER INFORMATION: Xaa is Lys(gamma-Glu-palmitoyl)

<400> SEQUENCE: 12

Xaa Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 13
<211> LENGTH: 42
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio alanine

<400> SEQUENCE: 13

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 14
<211> LENGTH: 37
```

```
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio serine

<400> SEQUENCE: 14

Xaa Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 15
<211> LENGTH: 32
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 15

Ser Xaa Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 16
<211> LENGTH: 30
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio dimethyl glycine
<220> FEATURE:
<221> NAME/KEY: MISC_FEATURE
<222> LOCATION: (29)..(29)
<223> OTHER INFORMATION: Xaa is dimethyl glycine

<400> SEQUENCE: 16

Xaa Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 17
<211> LENGTH: 30
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio alanine
```

```
<220> FEATURE:
<221> NAME/KEY: MISC_FEATURE
<222> LOCATION: (3)..(3)
<223> OTHER INFORMATION: Xaa is t-butyl glycine

<400> SEQUENCE: 17

Xaa Xaa Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 18
<211> LENGTH: 30
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio alanine
<220> FEATURE:
<221> NAME/KEY: MISC_FEATURE
<222> LOCATION: (3)..(3)
<223> OTHER INFORMATION: Xaa is beta, beta-dimethyl aspartic acid

<400> SEQUENCE: 18

Xaa Xaa Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 19
<211> LENGTH: 30
<212> TYPE: PRT
<213> ORGANISM: Homo sapiens

<400> SEQUENCE: 19

Phe Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 20
<211> LENGTH: 30
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio alanine

<400> SEQUENCE: 20

Phe Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 21
<211> LENGTH: 29
<212> TYPE: PRT
<213> ORGANISM: Homo sapiens

<400> SEQUENCE: 21
```

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 22
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio serine

<400> SEQUENCE: 22

```
Xaa Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 23
<211> LENGTH: 36
<212> TYPE: PRT
<213> ORGANISM: Homo sapiens

<400> SEQUENCE: 23

```
Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35
```

<210> SEQ ID NO 24
<211> LENGTH: 36
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 24

```
Tyr Xaa Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35
```

<210> SEQ ID NO 25
<211> LENGTH: 36
<212> TYPE: PRT
<213> ORGANISM: Homo sapiens

<400> SEQUENCE: 25

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Ile Asn Leu Ile Thr
            20                  25                  30
```

```
Arg Gln Arg Tyr
        35

<210> SEQ ID NO 26
<211> LENGTH: 36
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is thio proline

<400> SEQUENCE: 26

Tyr Xaa Ile Lys Pro Glu Ala Pro Gly Glu Asp Ala Ser Pro Glu Glu
1               5                   10                  15

Leu Asn Arg Tyr Tyr Ala Ser Leu Arg His Tyr Ile Asn Leu Ile Thr
            20                  25                  30

Arg Gln Arg Tyr
        35

<210> SEQ ID NO 27
<211> LENGTH: 36
<212> TYPE: PRT
<213> ORGANISM: Homo sapiens

<400> SEQUENCE: 27

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 28
<211> LENGTH: 36
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 28

Ala Xaa Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 29
<211> LENGTH: 68
<212> TYPE: PRT
<213> ORGANISM: Homo sapiens

<400> SEQUENCE: 29

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45
```

```
Val Cys Ala Asn Pro Glu Lys Lys Trp Val Arg Glu Tyr Ile Asn Ser
    50                  55                  60

Leu Glu Met Ser
65

<210> SEQ ID NO 30
<211> LENGTH: 68
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 30

Ser Xaa Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 31
<211> LENGTH: 68
<212> TYPE: PRT
<213> ORGANISM: Homo sapiens

<400> SEQUENCE: 31

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp
65

<210> SEQ ID NO 32
<211> LENGTH: 68
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 32

Gln Xaa Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
```

Asp His Leu Asp
65

<210> SEQ ID NO 33
<211> LENGTH: 76
<212> TYPE: PRT
<213> ORGANISM: Homo sapiens

<400> SEQUENCE: 33

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 34
<211> LENGTH: 76
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 34

Gln Xaa Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 35
<211> LENGTH: 76
<212> TYPE: PRT
<213> ORGANISM: Homo sapiens

<400> SEQUENCE: 35

Gln Pro Val Gly Ile Asn Thr Ser Thr Thr Cys Cys Tyr Arg Phe Ile
1               5                   10                  15

Asn Arg Lys Ile Pro Lys Gln Arg Leu Glu Ser Tyr Arg Arg Thr Thr
            20                  25                  30

Ser Ser His Cys Pro Lys Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 36
<211> LENGTH: 76
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 36

Gln Xaa Val Gly Ile Asn Thr Ser Thr Thr Cys Cys Tyr Arg Phe Ile
1               5                   10                  15

Asn Arg Lys Ile Pro Lys Gln Arg Leu Glu Ser Tyr Arg Arg Thr Thr
                20                  25                  30

Ser Ser His Cys Pro Lys Glu Ala Val Ile Phe Lys Thr Lys Leu Asp
            35                  40                  45

Lys Glu Ile Cys Ala Asp Pro Thr Gln Lys Trp Val Gln Asp Phe Met
50                  55                  60

Lys His Leu Asp Lys Lys Thr Gln Thr Pro Lys Leu
65                  70                  75

<210> SEQ ID NO 37
<211> LENGTH: 75
<212> TYPE: PRT
<213> ORGANISM: Homo sapiens

<400> SEQUENCE: 37

Gln Pro Asp Ala Leu Asn Ala Pro Val Thr Cys Cys Phe Thr Phe Ser
1               5                   10                  15

Ser Arg Lys Ile Ser Leu Gln Arg Leu Lys Ser Tyr Val Ile Thr Thr
                20                  25                  30

Ser Arg Cys Pro Gln Lys Ala Val Ile Phe Arg Thr Lys Leu Gly Lys
            35                  40                  45

Glu Ile Cys Ala Asp Pro Lys Glu Lys Trp Val Gln Asn Tyr Met Lys
50                  55                  60

His Leu Gly Arg Lys Ala His Thr Leu Lys Thr
65                  70                  75

<210> SEQ ID NO 38
<211> LENGTH: 75
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 38

Gln Xaa Asp Ala Leu Asn Ala Pro Val Thr Cys Cys Phe Thr Phe Ser
1               5                   10                  15

Ser Arg Lys Ile Ser Leu Gln Arg Leu Lys Ser Tyr Val Ile Thr Thr
                20                  25                  30

Ser Arg Cys Pro Gln Lys Ala Val Ile Phe Arg Thr Lys Leu Gly Lys
            35                  40                  45

Glu Ile Cys Ala Asp Pro Lys Glu Lys Trp Val Gln Asn Tyr Met Lys
50                  55                  60

His Leu Gly Arg Lys Ala His Thr Leu Lys Thr
65                  70                  75

<210> SEQ ID NO 39
<211> LENGTH: 38

<212> TYPE: PRT
<213> ORGANISM: Homo sapiens

<400> SEQUENCE: 39

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 40
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio serine

<400> SEQUENCE: 40

Xaa Xaa Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 41
<211> LENGTH: 28
<212> TYPE: PRT
<213> ORGANISM: Homo sapiens

<400> SEQUENCE: 41

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 42
<211> LENGTH: 28
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is histidine or phenylalanine
<220> FEATURE:
<221> NAME/KEY: MISC_FEATURE
<222> LOCATION: (2)..(2)
<223> OTHER INFORMATION: Xaa is thio serine

<400> SEQUENCE: 42

Xaa Xaa Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 43
<211> LENGTH: 44
<212> TYPE: PRT

<213> ORGANISM: Homo sapiens

<400> SEQUENCE: 43

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 44
<211> LENGTH: 44
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio alanine

<400> SEQUENCE: 44

Tyr Xaa Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 45
<211> LENGTH: 29
<212> TYPE: PRT
<213> ORGANISM: Homo sapiens

<400> SEQUENCE: 45

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 46
<211> LENGTH: 29
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio alanine

<400> SEQUENCE: 46

Tyr Xaa Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 47
<211> LENGTH: 5
<212> TYPE: PRT
<213> ORGANISM: Homo sapiens

<400> SEQUENCE: 47

Ala Pro Gly Pro Arg
1               5

<210> SEQ ID NO 48

```
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline

<400> SEQUENCE: 48

Ala Xaa Gly Pro Arg
1               5

<210> SEQ ID NO 49
<211> LENGTH: 44
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is (E)-hex-3-enoyltyrosine

<400> SEQUENCE: 49

Xaa Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 50
<211> LENGTH: 44
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is (E)-hex-3-enoyltyrosine
<220> FEATURE:
<221> NAME/KEY: MISC_FEATURE
<222> LOCATION: (2)..(2)
<223> OTHER INFORMATION: Xaa is thio alanine

<400> SEQUENCE: 50

Xaa Xaa Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 51
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is thio proline
<220> FEATURE:
<221> NAME/KEY: MISC_FEATURE
<222> LOCATION: (4)..(4)
<223> OTHER INFORMATION: Xaa is thio proline

<400> SEQUENCE: 51

Ala Xaa Gly Xaa Arg
1               5
```

```
<210> SEQ ID NO 52
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (8)..(8)
<223> OTHER INFORMATION: Xaa is L-(7-methoxycoumarin-4-yl)alanine

<400> SEQUENCE: 52

Xaa Leu Leu Lys Ala Ala Ala Xaa
1               5

<210> SEQ ID NO 53
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (2)..(2)
<223> OTHER INFORMATION: Xaa is thio Leucine
<220> FEATURE:
<221> NAME/KEY: MISC_FEATURE
<222> LOCATION: (8)..(8)
<223> OTHER INFORMATION: Xaa is L-(7-methoxycoumarin-4-yl)alanine

<400> SEQUENCE: 53

Xaa Xaa Leu Lys Ala Ala Ala Xaa
1               5

<210> SEQ ID NO 54
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (3)..(3)
<223> OTHER INFORMATION: Xaa is thio Leucine
<220> FEATURE:
<221> NAME/KEY: MISC_FEATURE
<222> LOCATION: (8)..(8)
<223> OTHER INFORMATION: Xaa is L-(7-methoxycoumarin-4-yl)alanine

<400> SEQUENCE: 54

Xaa Leu Xaa Lys Ala Ala Ala Xaa
1               5

<210> SEQ ID NO 55
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (4)..(4)
<223> OTHER INFORMATION: Xaa is thio Arginine
<220> FEATURE:
<221> NAME/KEY: MISC_FEATURE
```

```
<222> LOCATION: (8)..(8)
<223> OTHER INFORMATION: Xaa is L-(7-methoxycoumarin-4-yl)alanine

<400> SEQUENCE: 55

Xaa Leu Leu Xaa Ala Ala Ala Xaa
1               5

<210> SEQ ID NO 56
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (5)..(5)
<223> OTHER INFORMATION: Xaa is thio alanine
<220> FEATURE:
<221> NAME/KEY: MISC_FEATURE
<222> LOCATION: (8)..(8)
<223> OTHER INFORMATION: Xaa is L-(7-methoxycoumarin-4-yl)alanine

<400> SEQUENCE: 56

Xaa Leu Leu Lys Xaa Ala Ala Xaa
1               5

<210> SEQ ID NO 57
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (6)..(6)
<223> OTHER INFORMATION: Xaa is thio analine
<220> FEATURE:
<221> NAME/KEY: MISC_FEATURE
<222> LOCATION: (8)..(8)
<223> OTHER INFORMATION: Xaa is L-(7-methoxycoumarin-4-yl)alanine

<400> SEQUENCE: 57

Xaa Leu Leu Lys Ala Xaa Ala Xaa
1               5

<210> SEQ ID NO 58
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-(7-methoxycoumarin-4-yl)alanine
<220> FEATURE:
<221> NAME/KEY: MISC_FEATURE
<222> LOCATION: (7)..(7)
<223> OTHER INFORMATION: Xaa is thio analine
<220> FEATURE:
<221> NAME/KEY: MISC_FEATURE
<222> LOCATION: (8)..(8)
<223> OTHER INFORMATION: Xaa is L-(7-methoxycoumarin-4-yl)alanine

<400> SEQUENCE: 58

Xaa Leu Leu Lys Ala Ala Xaa Xaa
1               5

<210> SEQ ID NO 59
```

```
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is thio leucine
<220> FEATURE:
<221> NAME/KEY: MISC_FEATURE
<222> LOCATION: (6)..(6)
<223> OTHER INFORMATION: Xaa is L-(7-methoxycoumarin-4-yl)alanine

<400> SEQUENCE: 59

Xaa Leu Lys Ala Ala Xaa
1               5

<210> SEQ ID NO 60
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is thio leucine
<220> FEATURE:
<221> NAME/KEY: MISC_FEATURE
<222> LOCATION: (9)..(9)
<223> OTHER INFORMATION: Xaa is L-(7-methoxycoumarin-4-yl)alanine

<400> SEQUENCE: 60

Ala Lys Gly Xaa Ala Ala Phe Ala Xaa
1               5

<210> SEQ ID NO 61
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is L-(7-methoxycoumarin-4-yl)alanine

<400> SEQUENCE: 61

Ala Lys Gly Leu Ala Ala Phe Ala Xaa
1               5
```

METHOD OF STABILIZING A BIOACTIVE PEPTIDE AGAINST PROTEASE HYDROLYSIS

CROSS-REFERENCE TO RELATED APPLICATION

The present application is a continuation of, and claims priority to, U.S. patent application Ser. No. 15/305,681, filed Oct. 21, 2016, now allowed, which is a 35 U.S.C. § 371 national phase application from, and claims priority to, International Application No. PCT/US2015/028008, filed Apr. 28, 2015, and published under PCT Article 21(2) in English, which claims priority under 35 U.S.C. § 119(e) to U.S. Provisional Application No. 61/985,045, filed Apr. 28, 2014, all of which applications are incorporated herein by reference in their entireties.

SEQUENCE LISTING

The present application contains a Sequence Listing which has been submitted in ASCII format via EFS-Web and is hereby incorporated by reference in its entirety. Said ASCII copy, created on Dec. 4, 2018, is named 046483-7016US2_Sequence_Listing.txt and is 28.3 kilobytes in size.

BACKGROUND OF THE INVENTION

In recent years, there has been significant interest in the development of biologic drugs, including peptide biologics (Multard, 2013, Nat. Rev. Drug Discovery 12:329-332; Projan, et al., 2004, Expert Opin. Biol. Therapy 4:1345-1350; Verdine, et al., 2007, Clin. Cancer Res. 13:7264-7270). Peptide biologics have distinct advantages over small molecule drugs. Biologics are typically based on natural bioactive peptides (such as hormones and neuropeptides), and this makes the identification of a "lead compound" much easier than the identification of a small molecule lead compound (Buse, et al., 2009, Lancet 374:39-47; Kreymann, et al., 1987, Lancet 330:1300-1304).

Unfortunately, peptides generally make poor drugs because they undergo rapid proteolysis in vivo, leading to unfavorable pharmacokinetics (Weber, 2004, J. Med. Chem. 47:4135-4141). As a consequence, much of the time in development of peptide biologics is spent on modifying the peptide to reduce proteolysis, while maintaining biological activity (Buse, et al., 2009, Lancet 374:39-47; DeFronzo, et al., 2005, Diabetes Care 28:1092-1100). Some of the strategies reported in the art make use of the incorporation of unnatural amino acids (such as D-amino acids or β-amino acids) into the peptidic chain to overcome proteolysis (Bird, et al., 2010, Proc. Natl. Acad. Sci. 107:14093-14098; Sato, et al., 2006, Curr. Opin. Biotechnol. 27:638-642). Such approaches require identification of appropriate modification sites and are generally time consuming and often met with failure.

Heart disease is two times more common among obese adults and four times more common among diabetic adults, and consistently these conditions affect large numbers of U.S. adults, where 35% of adults are obese and 27% of those 65 and older have diabetes (90% of diabetes cases are Type 2). Both conditions are strongly regulated by peptide hormones and thus amenable to therapeutic intervention. Aside from insulin and glucagon, one of the most well characterized peptides in this class is the gut-derived incretin hormone glucagon-like peptide 1 (GLP-1) (Kreymann, et al., 1987, Lancet 330:1300-1304).

The GLP-1 7-36 residue fragment, which is referred to simply as "GLP-1" hereinafter (SEQ ID NO:1), stimulates insulin and suppresses glucagon secretion, inhibits gastric emptying, and reduces appetite and food intake (Drucker, et al., 2006, Lancet 368:1696-1705). Glucose-stimulated insulin secretion (GSIS) is a phenomenon wherein certain compounds (natural or synthetic) augment the release of insulin from pancreatic β-cell islets in the presence of glucose. These reagents have no effect on insulin secretion in the absence of glucose, and display two advantages over direct stimulators of insulin secretion. First, since they only cause increased insulin secretion in the presence of glucose, they augment the natural physiological mechanism for insulin secretion. Second, compounds that directly stimulate insulin secretion can cause β-cell stress and lead to the death of these vital cells (Maedler, et al., 2005, J. Clin. Endocrinol. Metab. 90:501-506). However, simple treatment by GLP-1 injection is not feasible because it is inactivated through proteolytic cleavage by dipeptidyl peptidase 4 (DPP-4) with a half-life of less than 2 minutes (Kim, et al., 2008, Pharmacol. Rev. 60:470-512). DPP-4 preferentially cleaves after Pro or Ala residues penultimate to the N-terminus and functions as the principal determinant of the circulating half-life for GLP-1 and many other peptides that affect cardiac health (Mentlein, et al., 1993, Eur. J. Biochem. 214:829-835).

Therapeutic approaches for enhancing incretin action include both degradation-resistant GLP-1 receptor (GLP-1R) agonists and inhibitors of DPP-4 activity. Two stabilized incretin mimetics are currently prescribed as injectables taken between once daily and once weekly: exenatide (Byetta®, SEQ ID NO:3) and liraglutide (Victoza®, SEQ ID NO:4). Both induce reductions in fasting, postprandial blood glucose concentrations and hemoglobin A1c (1-2%), which is associated with weight loss (2-5 kg). These incretin mimetics also expand pancreatic β-cell mass, and have emerged, along with DPP-4 inhibitors such as sitagliptin (Januvia®), as viable treatments for Type 2 diabetes (Drucker, et al., 2006, Lancet 368:1696-1705). While they act along the same hormone signaling axis, the two types of therapies are not mutually exclusive, as DPP-4 inhibitors fail to produce some desirable effects of the peptidomimetics such as appetite suppression and weight loss. Moreover, there is concern that DPP-4 inhibition could increase the risk of cancer (Stulc, et al., 2010, Diabetes Res. Clin. Pract. 88:125-131). DPP-4 exists as both a membrane bound form and a soluble form in circulation due to cleavage of the active site domain from the membrane. Activity of the membrane bound form suppresses non-small cell lung carcinoma cells (Wesley, et al., 2004, Int. J. Cancer 109:855-866). Given that there are concerns about chronic DPP-4 inhibition and some effects are unique to stabilized GLP-1 peptides, there is an interest in using peptides instead of, or in addition to, approved DPP-4 inhibitors.

DPP-4 substrates include not only GLP-1, but also glucose-dependent insulinotropic factor (GIP; SEQ ID NO:5), oxyntomodulin (OXM; SEQ ID NO:6), and brain natriuretic peptide (BNP; SEQ ID NO:7). All of these peptides have half-lives of less than 15 minutes. Similar to GLP-1, the hormones GIP and OXM act as glucose-lowering agents and have been studied extensively as diabetes treatments (Meneilly, et al., 1993, Diabetes Care 16:110-114; Cohen, et al., 2003, J. Clin. Endocrinol. Metab. 88:4696-4701). BNP plays an important role in the body's defense against hypertension and is used as a treatment of congestive heart failure (Del Ry, et al., 2013, Pharmacol. Res. 76:190-198; Grantham, et al., 1997, Am. J. Physiol.-Reg. Int. Comp. Physiol. 272:R1077-R1083). DPP-4 inhibition affects the levels of all of these peptides in circulation. On the other hand, stabilized versions of GIP, OXM, or BNP should act more selectively than DPP-4 inhibition, by impacting only one signaling pathway.

A variety of peptidomimetic strategies have already been applied to stabilizing peptide hormones, including GLP-1. Most of the strategies involve restricting DPP-4 access to the cleavable bond. Exenatide does this using replacement with other natural amino acids. Liraglutide includes a fatty acid modified sidechain, which wraps around the peptide and stabilizes a compact conformation. In the known peptides M1 (SEQ ID NO:8; Deacon, et al., 1998, Diabetologia 41:271-278); M2 (SEQ ID NO:9; Heard, et al., 2013, J. Med. Chem. 56:8339-8351) and M3 (SEQ ID NO:10; Iltz, et al., 2006, Clin. Ther. 28:652-665), access to cleavable bonds is blocked and conformations are stabilized with methyl substitutions. These modifications can extend the half-life for DPP-4 proteolysis, but can compromise GLP-1R affinity (for example, the minimalist M3 has a 6-fold lower affinity; Iltz, et al., 2006, Clin. Ther. 28:652-665). Modifications that increase GLP-1 half-life while sacrificing GLP-1R activation are less effective at achieving the desired effects of regulating glucose and promoting weight loss.

There is a need in the art for straightforward methods of stabilizing peptides, such as peptide hormones or neuropeptides, against proteolytic degradation in vivo. Such methods should allow for the identification of a modified peptide with similar potency to, but increased stability over, the naturally occurring peptide. The present invention addresses this unmet need in the art.

BRIEF SUMMARY OF THE INVENTION

The invention relates to unexpected discovery of thioamide-modified peptides that have long half-lives and are resistant to in vivo proteolytic degradation. In one aspect, the invention includes a peptide, or a salt or solvate thereof, comprising at least one selected from the group consisting of SEQ ID NOs:2, 11-18, 20, 22, 24, 26, 28, 30, 32, 34, 36, 38, 40, 42, 44, 46, 48 and 50-51. In certain embodiments, the C-terminus of the peptide is amide protected.

In yet another aspect, the invention includes a pharmaceutical composition comprising at least one peptide of SEQ ID NOs:2, 11-18, 20, 22, 24, 26, 28, 30, 32, 34, 36, 38, 40, 42, 44, 46, 48 and 50-51, and a pharmaceutically acceptable carrier. The pharmaceutical composition may further comprise at least one additional agent useful for treating or preventing a disease or disorder in a subject, which in certain embodiments is a human. The additional agent may be co-formulated with the thioamide-modified peptides. The disease or disorder includes, but is not limited to, diabetes, obesity, hypertension or congestive heart failure. The composition is administered to the subject by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

In yet another aspect, the invention includes a method of stabilizing a peptide against protease hydrolysis. The method comprises modifying with a thioamide the peptide bond that a protease hydrolyzes. In certain embodiments, the protease comprises DPP-4. In other embodiments, the protease comprises carboxypeptidase. The peptides that can be modified by the method stated herein include, but are not limited to, glucagon-like peptide 1 (GLP-1), glucose-dependent insulinotropic factor (GIP), oxyntomodulin (OXM), glucagon, pituitary adenylate cyclase-activating peptide (PACAP), vasoactive intestinal peptide (VIP), growth-hormone-releasing hormone (GHRH), sermorelin (GRF), peptide YY (PYY), pancreatic polypeptide (PP), B-type natriuretic peptide (BNP), neuropeptide Y (NPY), enterostatin (ENT), RANTES (CCL5), CCL2, CCL8, CCL7, and CCL13. In certain embodiments, the thioamide modification is between the second and third amino acid residues from the N-terminus of the peptide.

In certain embodiments, the thioamide modification of the peptides of the invention retains substantially the same biological activities and structures of corresponding unmodified peptides, but extends the in vivo half-lives of unmodified peptides.

In yet another aspect, the invention includes a method of treating or preventing diabetes or obesity in a subject in need thereof. The method comprises administering to the subject a therapeutically effective amount of a thioamide-modified peptide. The thioamide-modified peptide comprises at least one selected from the group consisting of SEQ ID NOs:2, 11-14, 16-18, 20, 22, 48 and 51, or a salt or solvate thereof. The thioamide-modified peptide has at least one effect selected from the group consisting of stimulating insulin production in the subject, suppressing glucagon secretion in the subject, inhibiting gastric emptying in the subject, reducing appetite in the subject, and reducing food intake in a subject.

In yet another aspect, the invention includes a method of treating or preventing a cardiac disease or disorder in a subject in need thereof. In certain embodiments, the cardiac disease or disorder comprises hypertension or congestive heart failure. The method comprises administering to the subject a therapeutically effective amount of a thioamide-modified peptide of SEQ ID NO:15, or a salt or solvate thereof.

In yet another aspect, the invention includes a kit comprising a thioamide-modified peptide, and an instructional material for use thereof, wherein the instructional material comprises instructions for treating or preventing a disease or disorder in a subject using the thioamide-modified peptide.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

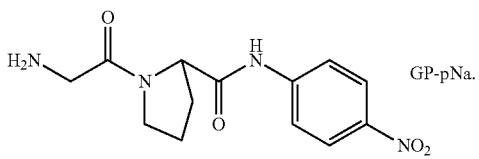 [SMILES: NCC(=O)N1CCCC1C(=O)Nc1ccc([N+](=O)[O-])cc1]

Figure 9:
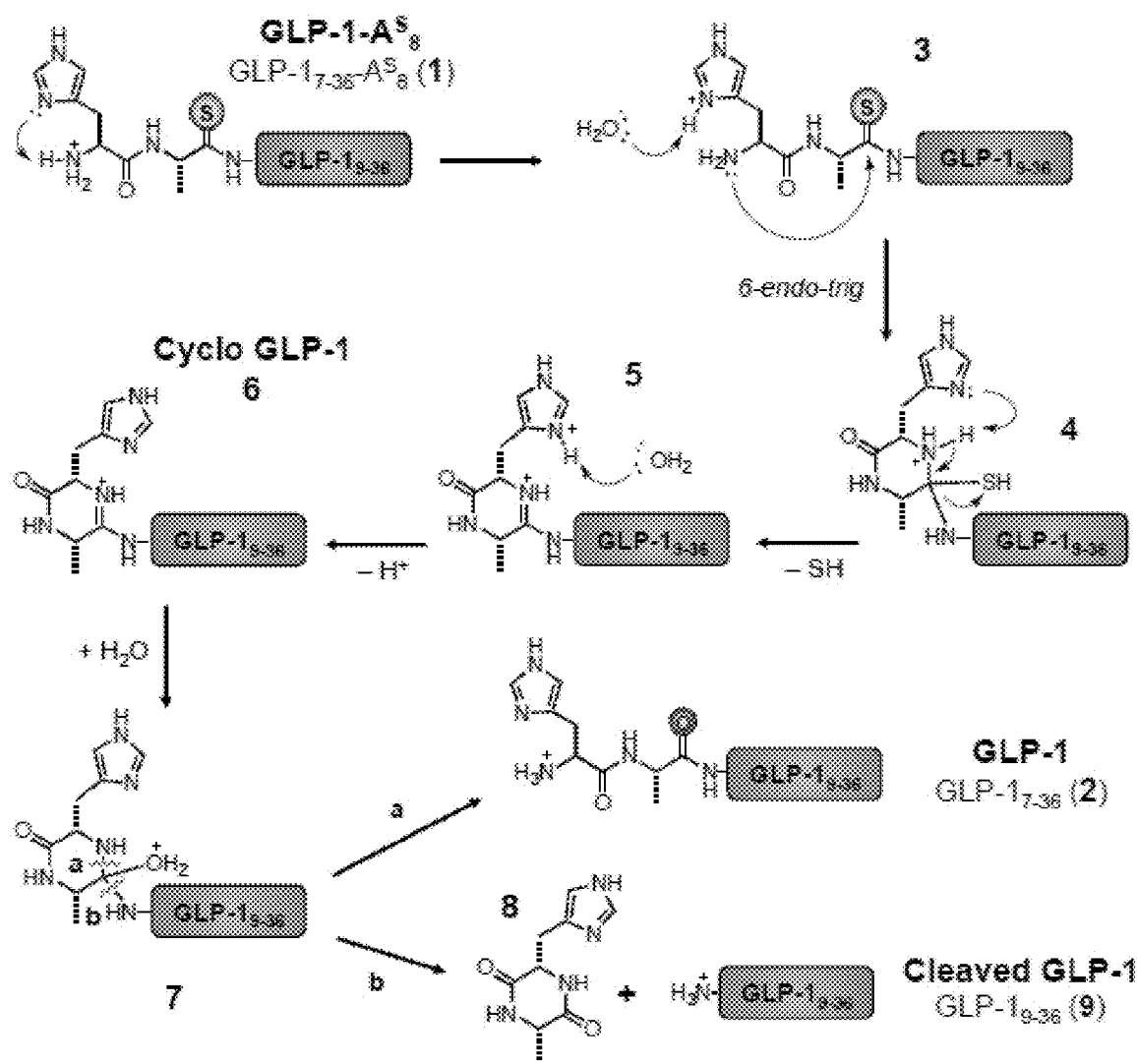

FIG. 9 illustrates a non-limiting mechanistic pathway of GLP-1-$A^s_8$ auto-degradation. Copper appeared to block auto-degradation.

Figure 10:
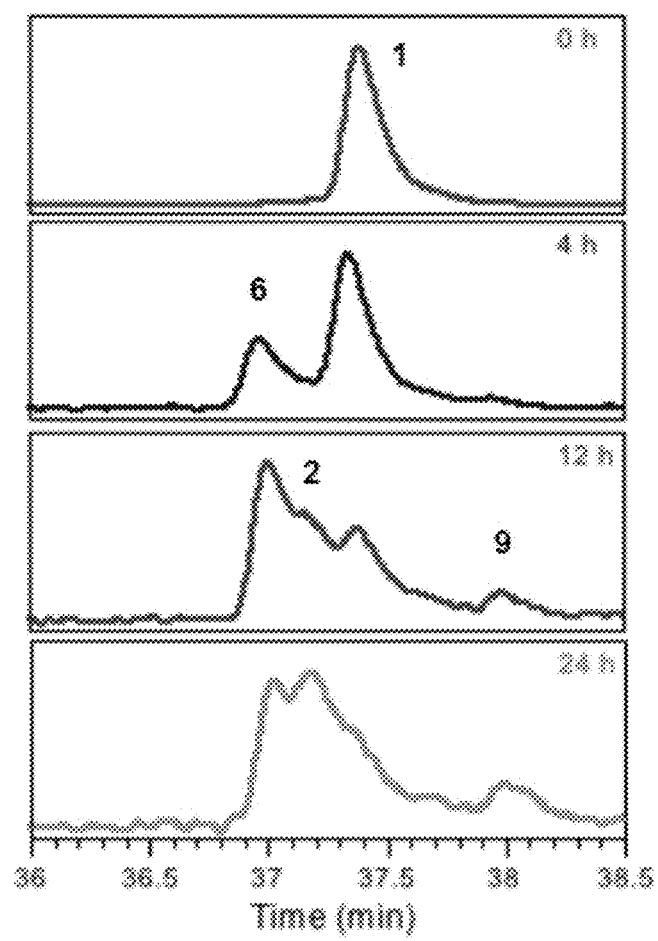

FIG. 10 comprises a set of graphs illustrating the time-dependent detection of GLP-1-$A^s_8$ auto-degradation.

Figure 11:
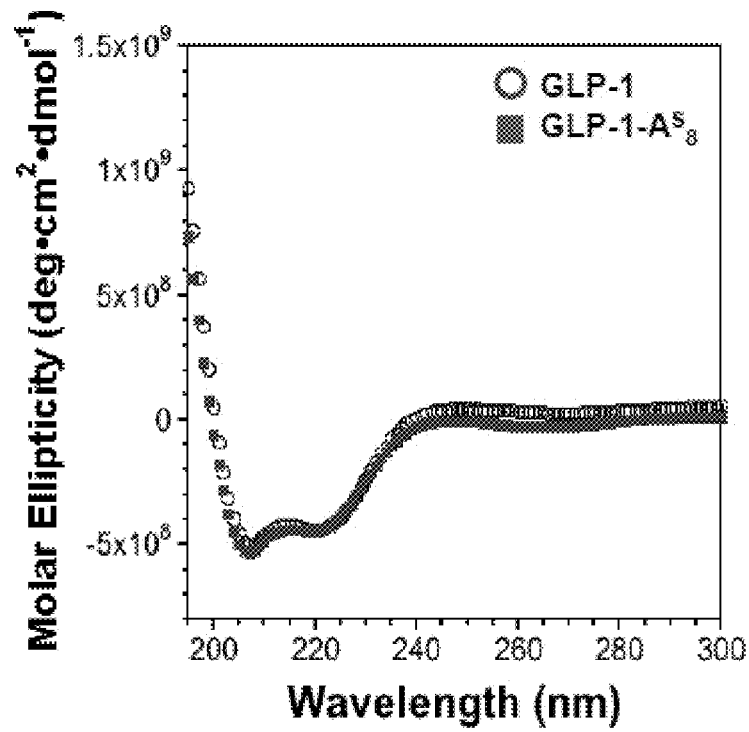

FIG. 11 is a graph illustrating the finding that the thioamide modification of a peptide (GLP-1-$A^s_8$) does not significantly alter the structure of the original peptide (GLP-1).

Figure 12:
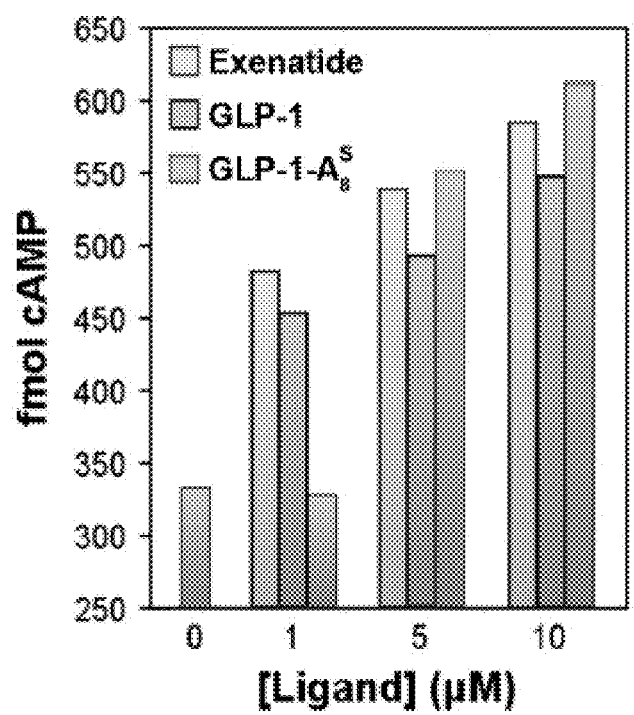

FIG. 12 is a graph illustrating the finding that GLP-1-$A^s_8$ activates cAMP production in GT1-7 neurons.

Figure 13:
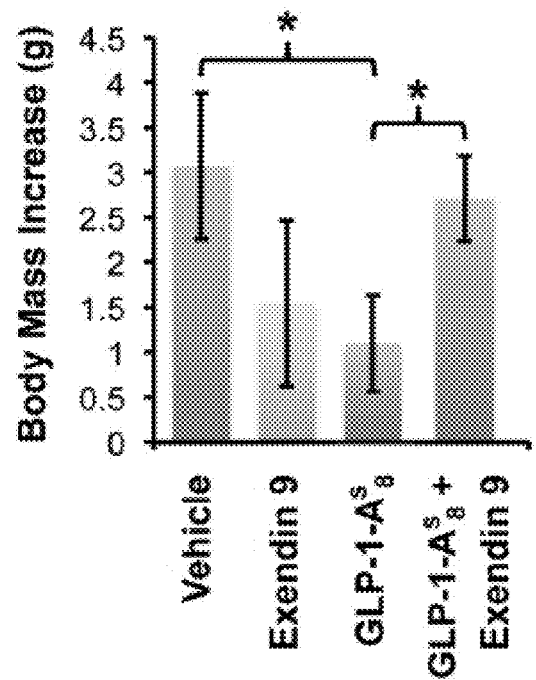

FIG. 13 is a graph illustrating that GLP-1-$A^s_8$ reduces body mass increase in rats. The rats experienced 15% reduction in food intake over 4 hours after i.p. injection. This effect was mitigated by co-injection of GLP-1-$A^s_8$ and Exendin-9.

Figure 14:
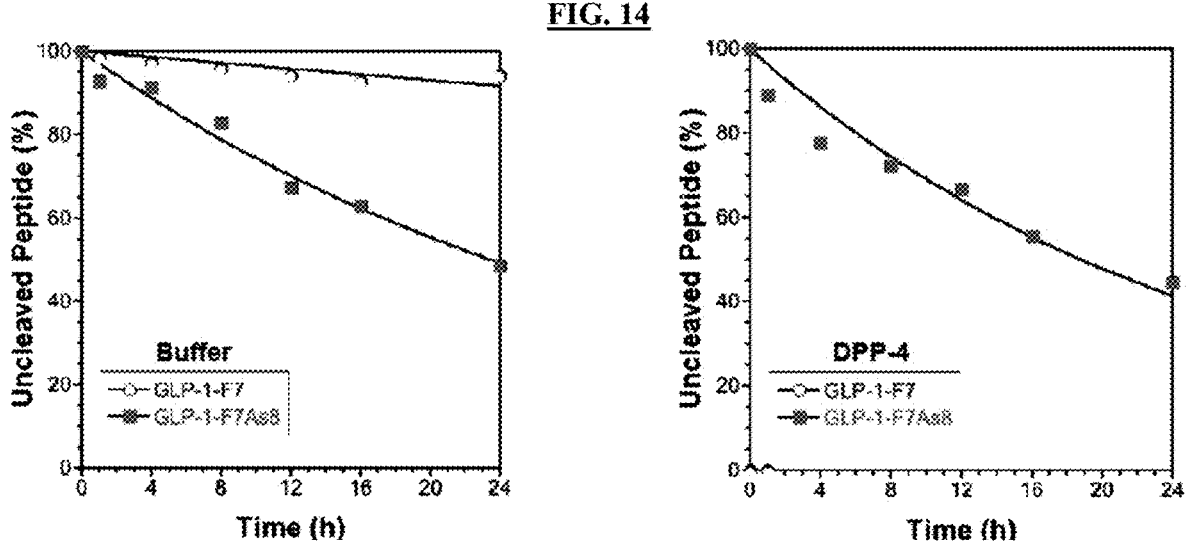

FIG. 14 comprises a set of graphs illustrating that GLP-1-F7$A^s_8$ is stable in buffer with or without DPP-4. The half-life of GLP-1-F7$A^s_8$ in buffer with or without DPP-4 is about 24 hours. GLP-1-F7$A^S_8$ was not degraded by DPP-4. $EC_{50}$s: GLP-1-F7=0.9 nM, GLP-1=0.8 nM.

Figure 15:
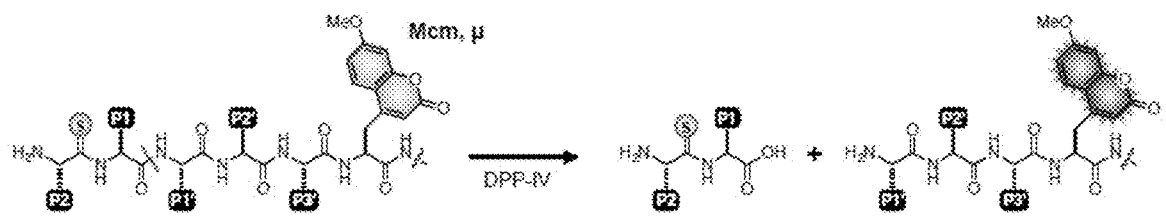

FIG. 15 illustrates the method of screening thioamide effects in presence of DPP-4. Short reporter peptides (containing Mcm, μ) allows for rapid screening at P1, P2 and P1' positions.

Figure 16:
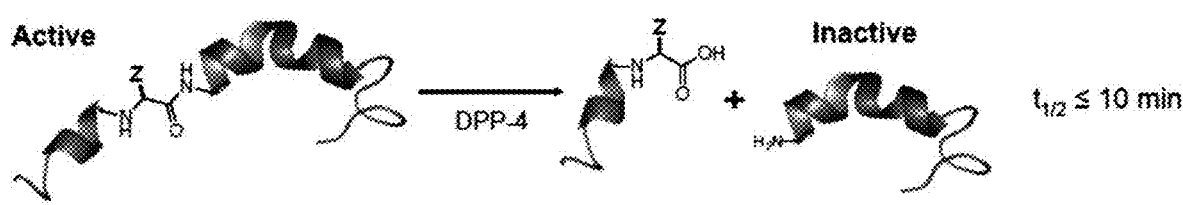

FIG. 16 illustrates the finding that GLP-1 is degraded by DPP-4, having a half-life less than 10 minutes.

Figure 17:
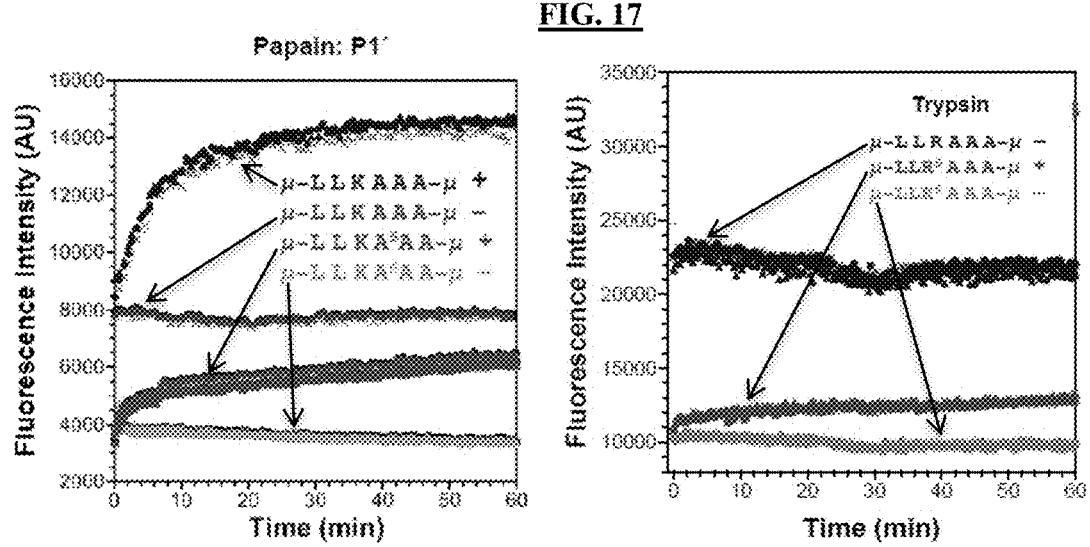
Figure 17:
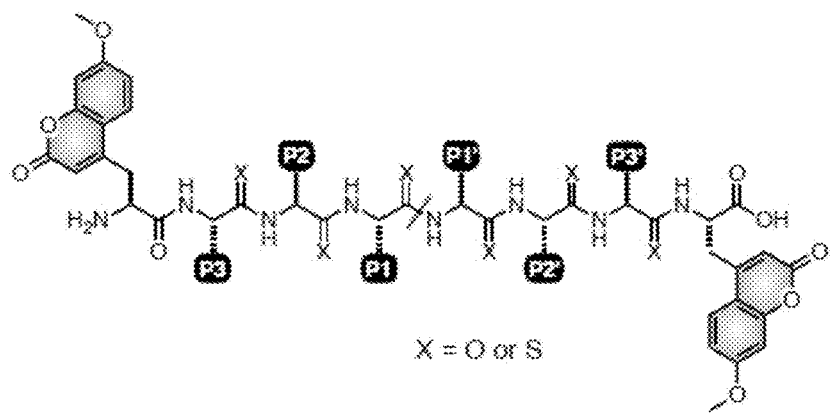

FIG. 17 illustrates systematic scanning of the effects of thioamide modification position in a peptide. The thioamide modifications were conducted at different positions of the peptide chain. The resulting peptides were mixed with either papain or trypsin enzymes to measure the changes of fluorescence intensity. The "+" sign after the peptide sequence means the presence of the corresponding enzyme. The "-" sign after the peptide sequence means the lack of the corresponding enzyme.

Figure 18:
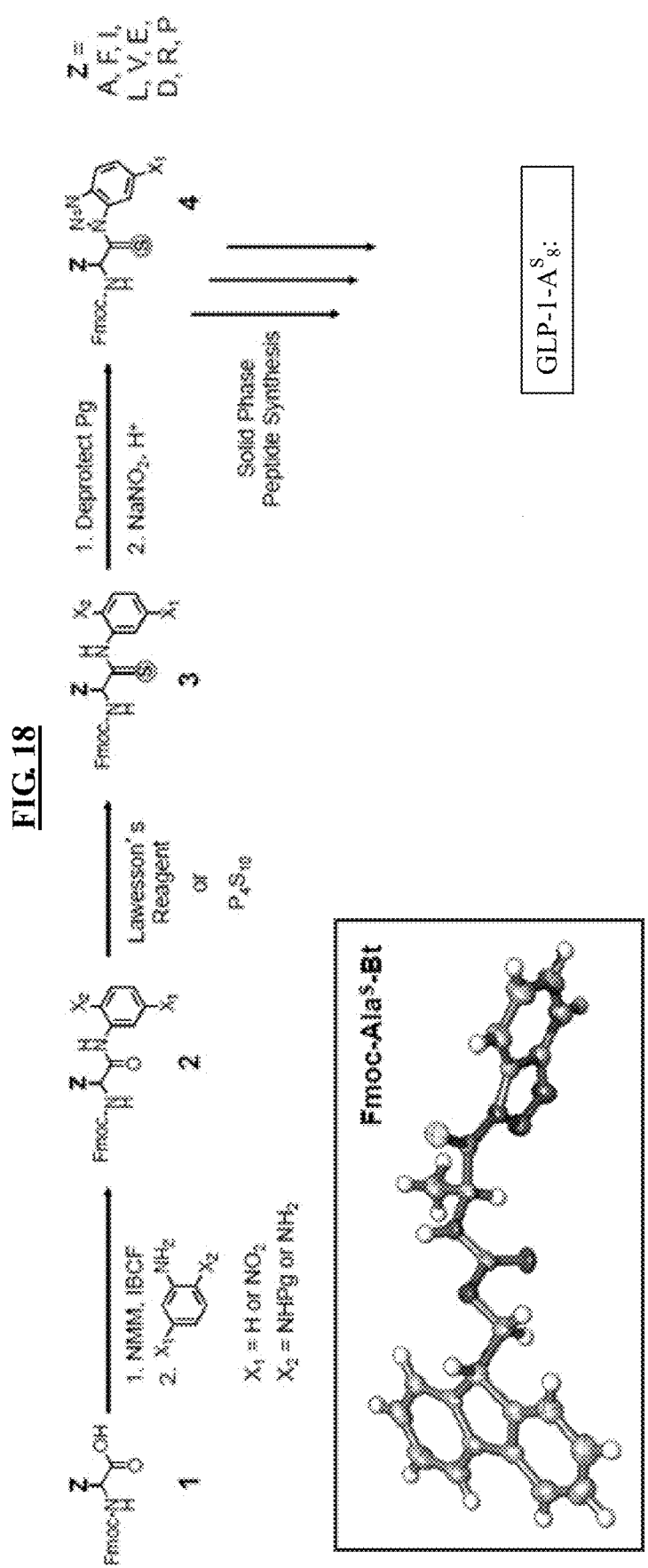

FIG. 18 comprises a non-limiting scheme to synthesize a thioamide peptide. GLP-1-$A^s_8$ is exemplified in the reaction scheme.

Figure 19:
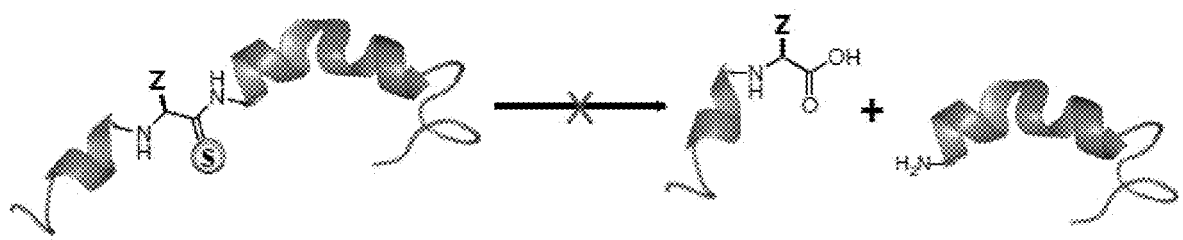
Figure 19:
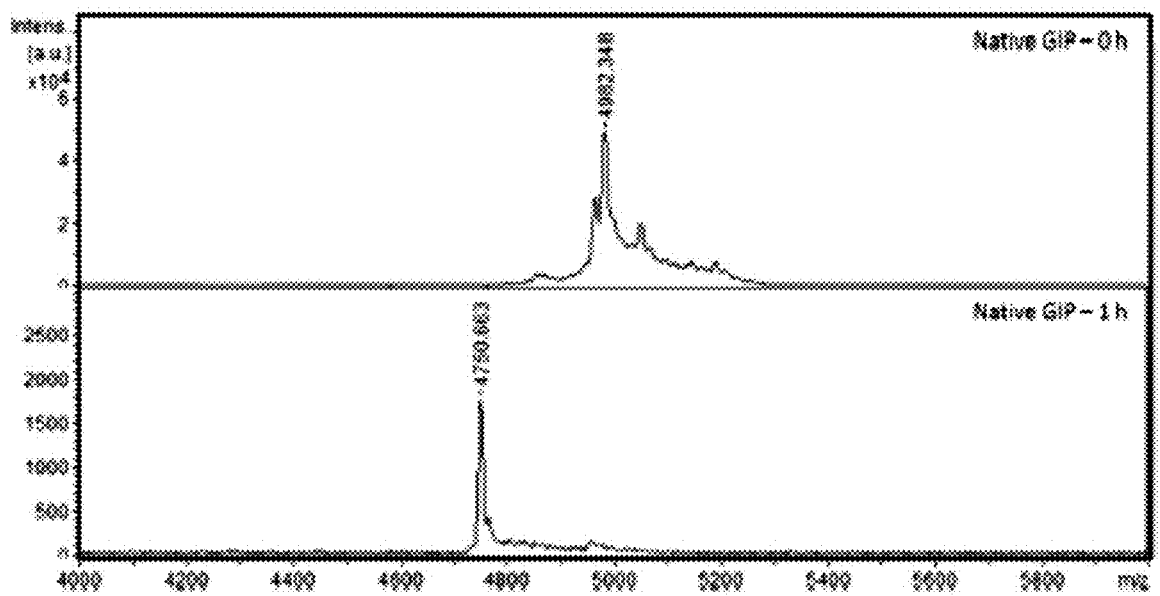
Figure 19:
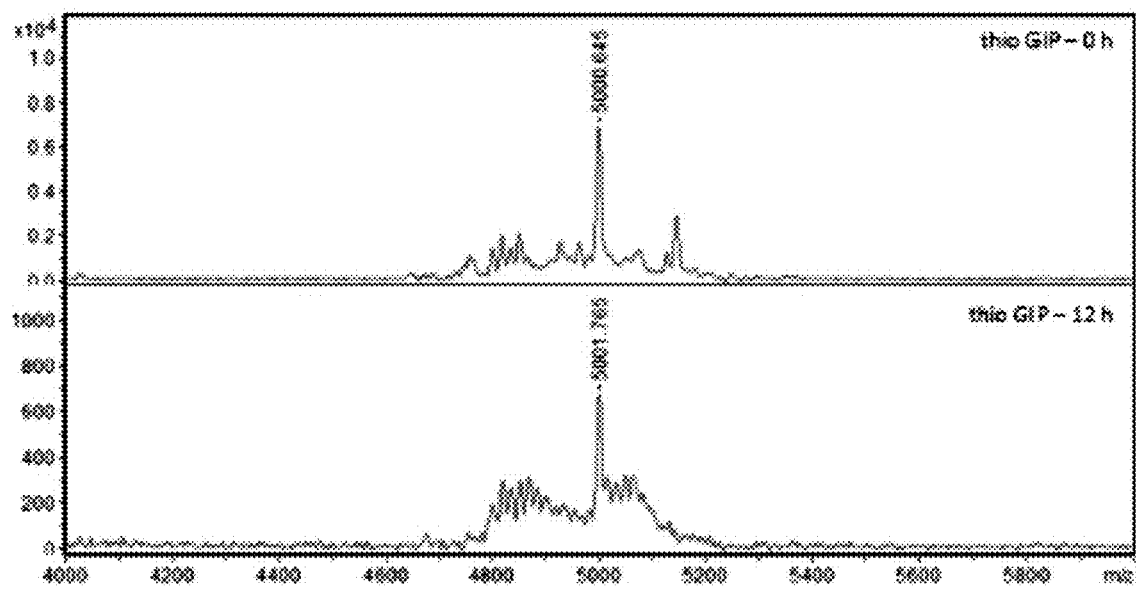

FIG. 19 illustrates the effects of thioamide modification at scissile bond position in glucose-dependent insulinotropic peptide (GIP) (GIP-$A^s_4$). Glucose-dependent insulinotropic peptide (GIP) stimulates pancreatic insulin secretion and fatty acid metabolism. GIP secretion is reduced in type 2 diabetes patients. Thioamide modification in GIP dramatically increase its proteolytic half-life to about 24 hours.

DETAILED DESCRIPTION OF THE INVENTION

In one aspect, the present invention relates to the use of thioamide modifications (0-to-S substitutions of the peptide bond) in biologically active peptides as a way to generate modified peptides that are stabilized against proteolytic degradation, and have approximately the same biological activity as the parent peptide. In certain embodiments, thioamide modification at the cleavage site of a peptide decreases proteolysis rates, in certain instances by as much as 1,000-fold, thus greatly improving the pharmacokinetics of the peptide. In other embodiments, thioamide modification of a peptide does not significantly alter the structure of the peptide and does not disrupt receptor binding or biological activity of the peptide. In yet other embodiments, thioamide modification of a peptide does not increase immune system recognition of the peptide as compared to the unmodified peptide.

As demonstrated herein, thioamide modification of biologically active peptides (such as GLP-1) stabilizes the peptide towards protease-mediated degradation without substantially altering their biological activities. In certain embodiments, the thioamide modified GLP-1 peptides of the invention stabilize the GLP-1 peptide towards proteolysis by proteases.

In certain embodiments, the thioamide-modified peptides of the invention have longer half-lives in vivo than the corresponding unmodified peptides. In other embodiments, the thioamide-modified peptides of the invention act as inhibitors of the proteases that cause proteolytic degradation of the corresponding unmodified peptides, in the case where the protease hydrolyzes the peptide bond that is replaced with the thioamide in the modified peptides.

In certain embodiments, in those cases wherein the thioamide modification is between the second and third amino acid residues from the N-terminus of the peptide and wherein the N-terminus residue of the peptide is histidine, the stability of thioamide-modified peptides is further increased by replacing the N-terminus residue with another amino acid, such as but not limited to, phenylalanine. In certain embodiments, the amino acid replacing the histidine does not comprises an imidazole side chain.

In certain embodiments, the thioamide-modified peptides of the invention are further modified, by using methods such as but not limited to: methylation of one or more NH groups in the peptide backbone; amidation and/or esterification of the C-terminus carboxyl group and/or any side chain carboxyl group; alkylation, acylation, carbamoylation and/or sulfonylation of the N-terminus amino group and/or any side chain amino group; and any other peptide modification known in the art.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "abnormal" when used in the context of organisms, tissues, cells or components thereof refers to those organisms, tissues, cells or components thereof that differ in at least one observable or detectable characteristic (e.g., age, treatment, time of day, and so forth) from those organisms, tissues, cells or components thereof that display the "normal" (expected) respective characteristic. Characteristics that are normal or expected for one cell or tissue type, might be abnormal for a different cell or tissue type.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "amino acid" refers to any natural or non-natural compound having a carboxyl group and an amino group in a molecule. An "amino acid" as used herein is meant to include both natural and synthetic amino acids, and both D- and L-amino acids. "Natural amino acid" means any of the twenty L-amino acids commonly found in naturally occurring peptides. "Non-natural amino acid residues" means any amino acid, other than the standard amino acids, regardless of whether it is prepared synthetically or derived from a natural source. As used herein, "synthetic amino acid" encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

As used herein, natural amino acids are represented by the full name thereof, by the three letter code corresponding thereto, or by the one-letter code corresponding thereto, as indicated below:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "BNP" refers to brain natriuretic peptide, and corresponds to the peptide of SEQ ID NO:7 or a salt or solvate thereof As used herein, the term "CD" refers to circular dichroism.

As used herein, the term "DPP-4" refers to dipeptidyl peptidase-4, adenosine deaminase complexing protein 2 or CD26 (cluster of differentiation 26). In certain embodiments, DPP-4 is mammalian, such as human.

As used herein, the term "exenatide" refers to the peptide of SEQ ID NO:3 or a salt or solvate thereof.

As used herein, the term "GIP" refers to glucose-dependent insulinotropic factor. In certain embodiments, the GIP is mammalian, such as human. In other embodiments, GIP comprises the peptide of SEQ ID NO:5 or a salt or solvate thereof.

As used herein, the term "GLP-1" refers to glucagon-like peptide-1 fragment 7-36. In certain embodiments, GLP-1 is human. In other embodiments, GLP-1 comprises the peptide of SEQ ID NO:1 or a salt or solvate thereof.

As used herein, the term "thio GLP-1" refers to GLP-1 wherein at least one peptidic bond is replaced with a thioamide. In certain embodiments, thio GLP-1 comprises the peptide of SEQ ID NO:2 or a salt or solvate thereof.

As used herein, an "instructional material" includes a publication, a recording, a diagram, or any other medium of expression that can be used to communicate the usefulness of a compound, composition, or method of the invention in the kit for effecting prevention or treatment of the various diseases or disorders recited herein. Optionally, or alternately, the instructional material can describe one or more methods of preventing or treating the diseases or disorders in a cell or a tissue of a mammal. The instructional material of the kit of the invention can, for example, be affixed to a container that contains the identified compound or composition of the invention or be shipped together with a container which contains the identified compound or composition. Alternatively, the instructional material can be shipped separately from the container with the intention that the instructional material and the compound or composition be used cooperatively by the recipient.

A "label" or "detectable label" or "tag" is a composition detectable by mass spectrometric, spectroscopic, photochemical, biochemical, immunochemical, or chemical means. For example, useful labels include radioactive isotopes (e.g., $^{3}H$, $^{35}S$, $^{32}P$, $^{51}Cr$ or $^{125}I$), stable isotopes (e.g., $^{13}$C, $^{15}$N or $^{18}$O), fluorescent dyes, electron-dense reagents, enzymes (e.g., alkaline phosphatase, horseradish peroxidase, or others commonly used in an ELISA), biotin, digoxigenin, or haptens or epitopes and proteins for which antisera or monoclonal antibodies are available. In general, a label as used in the context of the present invention is any entity that may be used to detect or isolate the product of interest. Thus, any entity that is capable of binding to another entity may be used in the practice of this invention, including without limitation, epitopes for antibodies, ligands for receptors, and nucleic acids, which may interact with a second entity through means such as complementary base pair hybridization.

As used herein, the term "ligation" as applied to two or more molecules refers to the process to creating covalent chemical bonds among the two or more molecules, as to form at least one molecule that incorporates at least a portion of each of the two or more molecules.

As used herein, the term "liraglutide" refers to the peptide of SEQ ID NO:4 (H-His-Ala-Glu-Gly-Thr-Phe-Thr-Ser-Asp-Val-Ser-Ser-Tyr-Leu-Glu-Gly-Gln-Ala-Ala-Lys(γ-Glu-palmitoyl)-Glu-Phe-Ile-Ala-Trp-Leu-Val-Arg-Gly-Arg-Gly-OH) or a salt or solvate thereof.

As used herein, the term "MALDI MS" refers to matrix-assisted laser desorption/ionization mass spectrometry.

As used herein, the term "OXM" refers to oxyntomodulin, corresponding to the peptide of SEQ ID NO:6 or a salt or solvate thereof.

The terms "patient," "subject," "individual," and the like are used interchangeably herein, and refer to any animal, or cells thereof whether in vitro or in situ, amenable to the methods described herein. In a non-limiting embodiment, the patient, subject or individual is a human.

The terms "peptide," "polypeptide" and "protein," as used herein, are interchangebly used to define as a chain of amino acid residues, usually having a defined sequence. As used herein, the term polypeptide is mutually inclusive of the terms "peptide" and "protein." "Polypeptide" also refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

Conventional notation is used herein to portray polypeptide sequences: the left-hand end of a polypeptide sequence is the amino-terminus; the right-hand end of a polypeptide sequence is the carboxyl-terminus. Peptidic bonds are formed by amides (also known as oxiamides).

"Proteases" (or "proteinases", "peptidases", or "proteolytic" enzymes) generally refer to a class of enzymes that cleave peptide bonds between amino acids of proteins. Because proteases use a molecule of water to effect hydrolysis of peptide bonds, these enzymes can also be classified as hydrolases. Six classes of proteases are presently known: serine proteases, threonine proteases, cysteine proteases, aspartic acid proteases, metalloproteases, and glutamic acid proteases (see, e.g., Barrett A. J. et al., The Handbook of Proteolytic Enzymes, 2$^{nd}$ ed. Academic Press, 2003). Proteases are involved in a multitude of physiological reactions from simple digestion of food proteins to highly regulated cascades (e.g., the cell cycle, the blood clotting cascade, the complement system, and apoptosis pathways). It is well known to the skilled artisan that proteases can break either specific peptide bonds, depending on the amino acid sequence of a protein, or break down a polypeptide to the constituent amino acids.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

A "therapeutic" treatment is a treatment administered to a subject who exhibits signs of pathology, for the purpose of diminishing or eliminating those signs.

A "therapeutically effective amount" or "effective amount" of a compound is that amount of compound that is sufficient to provide a beneficial effect to the subject to which the compound is administered. In certain embodiments, administration of a therapeutically effective amount of the compound prevents or treats (delays or prevents the onset of, prevents the progression of, inhibits, decreases or reverses) a disease or condition described herein, including alleviating symptoms of such diseases. An "effective amount" of a delivery vehicle is that amount sufficient to effectively bind or deliver a compound.

As used herein, the term "thioamide" refers to the group —C(=S)—NR—, wherein R is selected from the group consisting of H, optionally substituted alkyl, optionally substituted alkenyl, optionally substituted alkynyl, optionally substituted cycloalkyl, optionally substituted cycloalkenyl, optionally substituted cycloalkynyl, optionally substituted aryl, optionally substituted heteroaryl, and optionally substituted heterocyclyl. In certain embodiments, thioamides corresponds to amides (or oxiamides) wherein the carbonyl group of the amide bond is replaced with a thiocarbonyl group.

As used herein, the term "thioamide-modified" or "thioamide-substituted" peptide, polypeptide or protein refers to a peptide, polypeptide or protein wherein at least one peptide bond is replaced with a thioamide bond. In certain embodiments, the thioamide is located between the second and third amino acid residues from the N-terminus of the peptide, polypeptide or protein.

As used herein, an amino acid denoted as "AA*" comprises an amino acid AA that is thioamide-modified, wherein the carbonyl group of the amino acid is replaced with a thiocarbonyl. In certain embodiments, a protease cleaves a peptide at the dipeptide site AA1-AA2, wherein AA1 and AA2 are aminoacids. The protease cleaves the peptidic bond between AA1 and AA2 to form a N-terminus peptide fragment comprising AA1 as the C-terminus residue, and a C-terminus peptide fragment comprising AA2 as the N-terminus fragment. In other embodiments, the peptide comprising the dipeptide cleavage site AA1*-AA2 is cleaved by the protease at a lower rate than the peptide comprising the dipeptide cleavage site AA1-AA2.

For the purpose of notation used herein, the thioamide linkage between amino acid AA1 and amino acid AA2, wherein the thiocarbonyl group is derived from amino acid AA1 is denoted as AA1*-AA2. In this notation, the AA1 residue constitutes the N-terminus and the AA2 residue constitutes the C-terminus of the thioamide-modified dipeptide AA1*-AA2.

As used herein, "treating a disease or disorder" means reducing the frequency with which a symptom of the disease or disorder is experienced by a patient. Disease and disorder are used interchangeably herein.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In one aspect, the present invention relates to the use of thioamide modifications (O-to-S substitutions of the peptide bond) in biologically active peptides as a way to generate thioamide-modified peptides that are stabilized against proteolytic degradation, and have approximately the same biological activity as the parent peptide. In certain embodiments, thioamide modification at the cleavage site of a peptide decreases proteolysis rates by as much as 1,000-fold, thus greatly improving the pharmacokinetics of the peptide. In other embodiments, thioamide modification of a peptide does not significantly alter the structure of the peptide and does not disrupt receptor binding or biological activity of the peptide. In yet other embodiments, thioamide modification of a peptide does not increase immune system recognition of the peptide as compared to the unmodified peptide.

The peptide contemplated in the invention can be any peptide that is capable of undergoing to proteolytic degradation. In certain embodiments, the peptide is a dipeptidyl peptidase 4 (DPP-4) substrate or a carboxypeptidase substrate. The DPP-4 substrates include, but is not limited to, glucagon family peptides, pancreatic polypeptide family peptides, and chemokine family peptides.

Glucagon family peptides include, but are not limited to, glucagon (SEQ ID NO:21), pituitary adenylate cyclase-activating peptide (PACAP) (SEQ ID NO:39), vasoactive intestinal peptide (VIP) (SEQ ID NO:41), GLP-1 (SEQ ID NO:1), oxyntomodulin (OXM) (SEQ ID NO:6), GIP (SEQ ID NO:5), growth-hormone-releasing hormone (GHRH) (SEQ ID NO:43), sermorelin (GRF) (SEQ ID NO:45), and tesamorelin (SEQ ID NO:49).

Pancreatic polypeptide family peptides include, but are not limited to, peptide YY (PYY) (SEQ ID NO:25), pancreatic polypeptide (PP) (SEQ ID NO:27), B-type natriuretic peptide (BNP) (SEQ ID NO:7), neuropeptide Y (NPY) (SEQ ID NO:23), and enterostatin (ENT) (SEQ ID NO:47).

Chemokine family peptides include, but are not limited to, RANTES (CCL5) (SEQ ID NO:29), CCL2 (SEQ ID NO:31), CCL8 (SEQ ID NO:33), CCL7 (SEQ ID NO:35), and CCL13 (SEQ ID NO:37).

DPP-4 substrates play various important roles in regulating physiological and behavior activities, for example, insulin secretion (GLP-1, GIP), appetite (ENT), mood and stress (NPY), immune cell function (RANTES), and growth and development (GHRH). Several of these peptides are currently prescribed or under clinical trials in unmodified forms. In certain embodiments, modification with a thioamide residue at the indicated position should slow or eliminate proteolytic degradation by DPP-4. In other embodiments, degradation by other enzymes at other positions may also be limiting for in vitro or in vivo stability, and thioamide substitution at those position may further stabilize the peptide.

The hormones GIP, GLP-1, and OXM act as glucose-lowering agents and have been studied extensively as diabetes treatments.

Brain or B-type natriuretic peptide (BNP) is a 32-amino acid peptide secreted by the ventricles of the heart, causing a decrease in systemic vascular resistance and central venous pressure as well as an increase in natriuresis (lowering of sodium in the blood). BNP plays an important role in the body's defense against hypertension and is used as a treatment of congestive heart failure.

Growth-hormone-releasing hormone (GHRH), also known as growth-hormone releasing factor (GRF, GHRF), somatoliberin or somatocrinin, is produced in the arcuate nucleus of the hypothalamus. Semorelin is the truncated form of GHRH and is prescribed for growth hormone deficiency in children. Tesamorelin has an N-terminal modification of GHRH and is prescribed for lipodystrophy in HIV patients.

Neuropeptide Y (NPY) is a 36-amino acid peptide that acts as a neurotransmitter in the brain and in the autonomic nervous system. In the autonomic system it serves as a strong vasoconstrictor and causes fat accumulation. In the brain, it reduces anxiety and stress, as well as perception of pain.

Also, various DPP-4 substrates have short half-lives. For example, GLP-1, GIP, BNP, and OXM have in vivo half-lives of less than 15 minutes. NPY has a half-life of 15-20 minutes. ENT has a half-life of 5 minutes. GHRH has a half-life of 19 minutes.

DPP-4 inhibition affects the levels of these peptides in circulation as well as GLP-1. On the other hand, stabilized versions of GIP, OXM, GLP-1, NPY, GHRH, ENT, or BNP should act more selectively than DPP-4 inhibition, by impacting only one signaling pathway. In certain embodiments, the invention provides a thioamide-modified analog of a peptide, wherein the thioamide modification occurs at the peptidic bond that is cleaved by a protease. In other embodiments, the protease comprises DPP-4. In yet other embodiments, the protease comprises carboxypeptidase. In yet other embodiments, the peptide comprises a DPP-4 substrate. In certain instances, the peptide comprises GIP, OXM, GLP-1, NPY, GHRH, ENT, or BNP. In yet other embodiments, the thioamide modification reduces the rate at which the peptide is cleaved by the protease. In yet other embodiments, the peptide bond that is cleaved by the protease is subject to the thioamide modification. In yet other embodiments, a peptide bond that is neighboring to the peptide bond cleaved by the protease is subject to the thioamide modification.

As demonstrated herein in a non-limiting manner, the invention may be implemented using incretin hormone glucagon-like peptide 1 (GLP-1), which stimulates insulin and suppresses glucagon secretion, inhibits gastric emptying, and reduces appetite and food intake. GLP-1 is inactivated through proteolytic cleavage by dipeptidyl peptidase 4 (DPP-4) with a half-life of less than 2 minutes. Stabilized GLP-1 analogs exenatide (BYETTA®) and liraglutide (VICTOZA®) are currently prescribed as Type 2 diabetes drugs.

Figure 1:
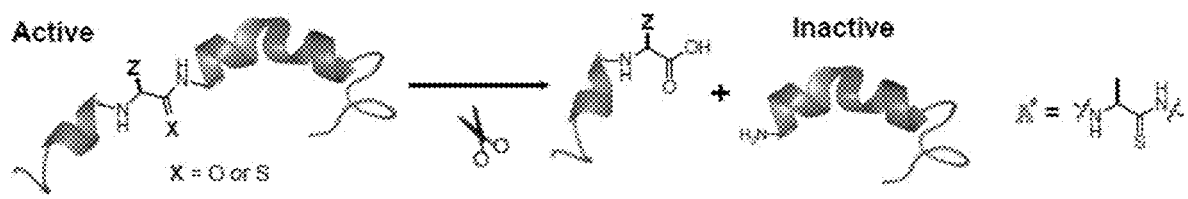
FIG. 1 illustrates peptide inactivation by DPP-4. Peptides are inactivated by DPP-4-catalyzed cleavage at the bond indicated with a slash. GLP-1 analogs such as exenatide, liraglutide, M1 (taspoglutide), M2, and M3 exhibit increased stability towards DPP-4 degradation. Modified residues relative to GLP-1 are shown in green.

As demonstrated herein, thioamide modification at the scissile bond of GLP-1 (thio GLP-1, X=S in FIG. 1, SEQ ID NO:2, wherein Xaa (1) is histidine) increased the GLP-1 half-life to ranges (>24 hours) comparable to exenatide and liraglutide. For this study, purified peptides were incubated with DPP-4 in assay buffer for various time periods. The reactions were quenched, and the products analyzed by HPLC/MALDI MS to determine the amount of intact peptide. The degradation data indicated that the half-life of thio GLP-1 is greater than about 24 hours under conditions where the half-life of GLP-1 is 21 minutes. Thus, an at least 100-fold increase in stability was obtained by introducing a single atom substitution in GLP-1.

To further investigate the interaction between DPP-4 and thio GLP-1, kinetic assays showed that thio GLP-1 acts as a competitive DPP-4 inhibitor. Thus, thio GLP-1 acts as both a stabilized GLP-1R agonist and a DPP-4 inhibitor. In certain embodiments, this unique attribute affects the in vivo pharmacology of thio GLP-1.

The effects of thioamide modification on the structure of GLP-1 were also studied. CD spectroscopy was used to examine the secondary structure of GLP-1 and thio GLP-1 in the far UV region, showing that the thioamide at $Ala_8$ was not disruptive to GLP-1 folding, since the CD signatures of thio GLP-1 and GLP-1 were identical.

Further, the activity of thio GLP-1 as compared to GLP-1 was tested in vivo using intra-peritoneal glucose tolerance tests (IPGTTs). In these experiments, mice were injected with the peptide 60 minutes prior to administration of a glucose challenge (time=0). Blood glucose levels were measured at −90, 0, 30, 60, 90 and 120 minutes. Thio GLP-1 greatly improved glucose tolerance and led to significantly lower blood glucose levels at every time point, to a greater degree than GLP-1. These data demonstrate that thio GLP-1 is active in mice.

As demonstrated herein in a non-limiting manner, the invention may also be implemented using glucose-dependent insulinotropic peptide (GIP) (SEQ ID NO:5). GIP stimulates pancreatic insulin secretion and fatty acid metabolism. GIP secretion is reduced in type 2 diabetes patients. Thioamide modification at the scissile position in GIP (GIP-$A^S_4$, SEQ ID NO:13) increase its proteolytic half-life dramatically to about 24 hours (FIG. 19).

Although the embodiments have demonstrated thioamide modification at the scissile bond of a peptide (such as a DPP-4 substrate), one of ordinary skill in the art would appreciate the thioamide modification can be at any position of the peptide under consideration. Thioamide modification at a different position from the scissile position in the DPP-4 substrate (or any other position thought to allow the peptide to be degraded by protease) may have distinct therapeutic effects. As such, thioamide modification at any possible position of the DPP-4 substrate is contemplated within the present invention.

It is also contemplated within the invention to have two or more thioamide modifications in a peptide. Such multiple thioamide modification can help stabilize the peptide against proteolytic degradation caused by DPP-4, as well as other proteases. One non-limiting example is enterostatin (ENT), expressed as a precursor protein in the pancreas, stomach, duodenal mucosa, and specific brain regions. ENT is a peptide having the sequence of $AP_2GP_4R$ (the subscripts are used to differentiate the positions of two Ps only), and selectively inhibits the intake of dietary fat in rodent models given a choice of diets. ENT is subject to DPP-4 proteolysis and carboxypeptidase at the $P_2$ and $P_4$ positions respectively. Accordingly, thioamide modifications at $P_2$ and $P_4$ positions make ENT more stable in the presence of DPP-4 and carboxypeptidase.

Compositions

The invention includes a thioamide-substituted peptide, wherein the peptide is modified with a thioamide at the peptidic bond that is cleaved by a protease.

In certain embodiments, the peptide comprises a peptide selected from the group consisting of:

```
SEQ ID NO: 2, wherein Xaa (1) is histidine(thio GLP-1):
HA*EGTFTSDVSSYLEGQAAKEFIAWLVKGR;

SEQ ID NO: 2, wherein Xaa (1) is phenylalanine (GLP-1-F7AS8):
FA*EGTFTSDVSSYLEGQAAKEFIAWLVKGR;

SEQ ID NO: 11, wherein Xaa (1) is histidine (thio exenatide):
HG*EGTFTSDLSKQMEEEAVRLFIEWLKNGGPSSGAPPS;

SEQ ID NO: 11, wherein Xaa (1) is phenylalanine:
FG*EGTFTSDLSKQMEEEAVRLFIEWLKNGGPSSGAPPS;

SEQ ID NO: 12, wherein Xaa (1) is histidine(thio liraglutide):
HA*EGTFTSDVSSYLEGQAAXEFIAWLVRGRG, [X = Lys(γ-Glu-palmitoyl)];

SEQ ID NO: 12, wherein Xaa (1) is phenylalanine:
FA*EGTFTSDVSSYLEGQAAXEFIAWLVRGRG, [X = Lys(γ-Glu-palmitoyl)];

SEQ ID NO: 13 (thio GIP):
YA*EGTFISDYSIAMDKIHQQDFVNWLLAQKGKKNDWKHNITQ;
```

-continued

SEQ ID NO: 14, wherein Xaa (1) is histidine (thio OXM):
HS*QGTFTSDYSKYLDSRRAQDFVQWLMNTKRNRNNIA;

SEQ ID NO: 14, wherein Xaa (1) is phenylalanine:
FS*QGTFTSDYSKYLDSRRAQDFVQWLMNTKRNRNNIA;

SEQ ID NO: 15 (thio BNP):
SP*KMVQGSGCFGRKMDRISSSSGLGCKVLRRH;

SEQ ID NO: 16, wherein Xaa (1) is histidine (thio M1):
Hα*EGTFTSDVSSYLEGQAAKEFIAWLVKαR, (α = dimethyl Gly);

SEQ ID NO: 16, wherein Xaa (1) is phenylalanine:
Fα*EGTFTSDVSSYLEGQAAKEFIAWLVKαR, (α = dimethyl Gly);

SEQ ID NO: 17, wherein Xaa (1) is histidine (thio M2):
HA*αGTFTSDVSSYLEGQAAKEFIAWLVKGR, (α = t-butyl Gly);

SEQ ID NO: 17, wherein Xaa (1) phenylalanine:
FA*αGTFTSDVSSYLEGQAAKEFIAWLVKGR, (α = t-butyl Gly);

SEQ ID NO: 18, wherein Xaa (1) is histidine (thio M3):
HA*αGTFTSDVSSYLEGQAAKEFIAWLVKGR, (α = β,β-D);

SEQ ID NO: 18, wherein Xaa (1) is phenylalanine:
FA*αGTFTSDVSSYLEGQAAKEFIAWLVKGR, (α = β,β-D);

SEQ ID NO: 22, wherein Xaa (1) is histidine (thio Glucagon):
HS*QGTFTSDYSKYLDSRRAQDFVQWLMNT;

SEQ ID NO: 22, wherein Xaa (1) is phenylalanine:
FS*QGTFTSDYSKYLDSRRAQDFVQWLMNT;

SEQ ID NO: 24 (thio NPY):
YP*SKPDNPGEDAPAEDMARYYSALRHYINLITRQRY;

SEQ ID NO: 26 (thio PYY):
YP*IKPEAPGEDASPEELNRYYASLRHYINLITRQRY;

SEQ ID NO: 28 (thio pancreatic polypeptide (PP)):
AP*LEPVYPGDNATPEQMAQYAADLRRYINNILTRPRY;

SEQ ID NO: 30 (thio RANTES (CCL5)):
SP*YSSDTTPCCFAYIARPLPRAHIKEYFYTSGKCSNPAVVFVTRKNRQVCANPEKKWVREYINSLEMS;

SEQ ID NO: 32 (thio CCL2):
QP*DAINAPVTCCYNFTNRKISVQRLASYRRITSSKCPKEAVIFKTIVAKEICADPKQKWVQDSMDHLD;

SEQ ID NO: 34 (thio CCL8):
QP*DSVSIPITCCFNVINRKIPIQRLESYTRITNIQCPKEAVIFKTKRGKEVCADPKERWVRDSMKHLDQIFQNLKP;

SEQ ID NO: 36 (thio CCL7):
QP*VGINTSTTCCYRFINRKIPKQRLESYRRTTSSHCPKEAVIFKTKLDKEICADPTQKWVQDFMKHLDKKTQTPKL;

SEQ ID NO: 38 (thio CCL13):
QP*DALNAPVTCCFTFSSRKISLQRLKSYVITTSRCPQKAVIFRTKLGKEICADPKEKWVQNYMKHLGRKAHTLKT;

SEQ ID NO: 40, wherein Xaa (1) is histidine(thio PACAP):
HS*DGIFTDSYSRYRKQMAVKKYLAAVLGKRYKQRVKNK;

SEQ ID NO: 40, Xaa (1) is phenylalanine:
FS*DGIFTDSYSRYRKQMAVKKYLAAVLGKRYKQRVKNK;

SEQ ID NO: 42, wherein Xaa (1) is histidine (thio vasoactive intestinal peptide (VIP)):
HS*DAVFTDNYTRLRKQMAVKKYLNSILN;

SEQ ID NO: 42, wherein Xaa (1) is phenylalanine:
FS*DAVFTDNYTRLRKQMAVKKYLNSILN;

SEQ ID NO: 44 (thio GHRH):
YA*DAIFTNSYRKVLGQLSARKLLQDIMSRQQGESNQERGARARL;

SEQ ID NO: 46 (thio GRF):
YA*DAIFTNSYRKVLGQLSARKLLQDIMSR;

```
SEQ ID NO: 48 (thio ENT):
AP*GPR;

SEQ ID NO: 50 (thio Tesamorelin):
Y#A*DAIFTNSYRKVLGQLSARKLLQDIMSRQQGESNQERGARARL;

SEQ ID NO: 51 (bithio ENT)
AP*GP*R;
``` wherein the C-terminus is optionally amide protected, and the amino acid marked as * is thioamide-modified; a salt or solvate thereof, and any combinations thereof.

The invention further comprises a pharmaceutical composition comprising at least one peptide of the invention and a pharmaceutically acceptable carrier.

Methods

The invention includes a method of stabilizing a peptide against protease hydrolysis, the method comprising modifying with a thioamide the peptidic bond that the protease hydrolyzes. In certain embodiments, the protease comprises DPP-4. In other embodiments, the thioamide is formed between the second and third amino acid residues from the N-terminus of the peptide. In yet other embodiments, the peptide comprises a DPP-4 substrate. In certain instances, the peptide comprises GLP-1, GIP, OXM, BNP, ENT, GHRH, NPY or any combinations thereof. In yet other embodiments, the thioamide-modified peptide has equivalent biological activity to the peptide. In yet other embodiments, the thioamide-modified peptide has longer in vivo half-life than the peptide.

The invention further includes a method of treating or preventing diabetes or obesity in a subject in need thereof, wherein the method comprises administering to the subject a therapeutically effective amount of a pharmaceutical composition comprising a thioamide-modified peptide. In certain embodiments, the thioamide-modified peptide comprises at least one selected from the group consisting of SEQ ID NOs:2, 11-14, 16-18, 20, 22, 48 51 or a salt or solvate thereof. In other embodiments, the thioamide-modified peptide has at least one effect selected from the group consisting of stimulate insulin production in the subject, suppress glucagon secretion in the subject, inhibit gastric emptying in the subject, reduce appetite in the subject, and reduce food intake in the subject.

The invention further includes a method of treating or preventing a cardiac disease or disorder in a subject in need thereof, wherein the method comprises administering to the subject a therapeutically effective amount of a pharmaceutical composition comprising a thioamide-modified peptide. In certain embodiments, the thioamide-modified peptide comprises SEQ ID NO:15, or a salt or solvate thereof. In other embodiments, the cardiac disease or disorder comprises hypertension or congestive heart failure.

Kits

The invention includes a kit comprising a thioamide-modified peptide of the invention, and an instructional material for use thereof. The instructional material comprises instructions for treating or preventing a disease or disorder in a subject using the thioamide-modified peptide of the invention. In certain embodiments, the kit further comprises at least one additional agent that treats or prevents the disease or disorder in the subject.

Combination Therapies

In certain embodiments, the compounds of the invention are useful in the methods of the invention in combination with at least one additional compound useful for treating or preventing a disease or disorder contemplated within the invention. This additional compound may comprise compounds identified herein or compounds, e.g., commercially available compounds, known to treat, prevent or reduce the symptoms of a disease or disorder contemplated within the invention.

For treatment or prevention of diabetes or obesity, the additional compound may be selected from the group consisting of GLP-1; GIP; OXM; meglitinides, such as repaglinide (PRANDIN®), and nateglinide (STARLIX®); sulfonylureas, such as glipizide (GLUCOTROL®), glimepiride (AMARYL®), and glyburide (DIABETA®, GLYNASE®); DPP-4 inhibitors, such as saxagliptin (ONGLYZA®), sitagliptin (JANUVIA®), and linagliptin (TRADJENTA®); biguanides, such as metformin (FORTAMET®, GLUCOPHAGE®, and others); thiazolidinediones, such as rosiglitazone (AVANDIA®) and pioglitazone (ACTOS®); alpha-glucosidase inhibitors, such as acarbose (PRECOSE®) and miglitol (GLYSET®); amylin mimetics, such as pramlintide (SYMLIN®); incretin mimetics, such as exenatide (BYETTA®) and liraglutide (VICTOZA®); insulin and insulin analogs and derivatives.

For treatment or prevention of a cardiac disorder or disease, the additional compound may be selected from the group consisting of aspirin, statins, thiazide-based diuretics, angiotensin converting enzyme inhibitors, angiotensin II receptor blockers, calcium channel blockers, vasodilators, aldosterone receptor antagonists, beta-blockers, and alpha-blockers.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient or subject, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/ per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include, but are not limited to, nasal, inhalational, topical, oral, buccal, rectal, pleural, peritoneal, vaginal, intramuscular, subcutaneous, transdermal, epidural, intratracheal, otic, intraocular, intrathecal or intravenous route. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 2003/0147952; 2003/0104062; 2003/0104053; 2003/0044466; 2003/0039688; and 2002/0051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

In these studies *Mus musculus*; lean and diet-induced obese, DIO, C57BL6/J mice are used. In certain embodiments, mice may be used to study the ability of the peptides of the invention to regulate blood glucose levels during a glucose tolerance test. Mice are injected intraperitoneally using 28 gauge insulin syringes with the peptides dissolved in saline, administered in a volume corresponding to 0.5% of body mass. Mice are monitored following compound administration for any signs of adverse reactions.

Thirty minutes after injection with the peptides, mice are injected intraperitoneally with a sterile solution of 20% D-glucose in saline (1-2 g/kg) using a 28 gauge insulin needle. Administered volume of the saline glucose solution does not exceed 1% of body mass (e.g., 0.3 mL for a 30 g mouse). Blood glucose measurements is performed just prior to injection of the peptide (−30 minutes), before glucose injection (0 minutes), and at 15, 30, 60, and 120 minutes after injection. Over the course of the 150 minute experiment, a total of 30 μL (5 μL per time point) of blood are collected. At the end of the measurement period, mice are sacrificed by $CO_2$ inhalation, and blood is collected to measure residual peptide levels. In addition, a similar set of experiments is performed, wherein the peptides are injected 300-360 minutes prior to glucose injection to determine whether thio peptide has a longer half-life than the parent peptide.

Male mice that are at least 16 weeks, but younger than 24 weeks old, are used. For each condition (thio peptide, peptide, and vehicle), 8 mice are used, for a total of 24 mice per experiment.

Example 1: Selected Thioamide Studies

Figure 2:
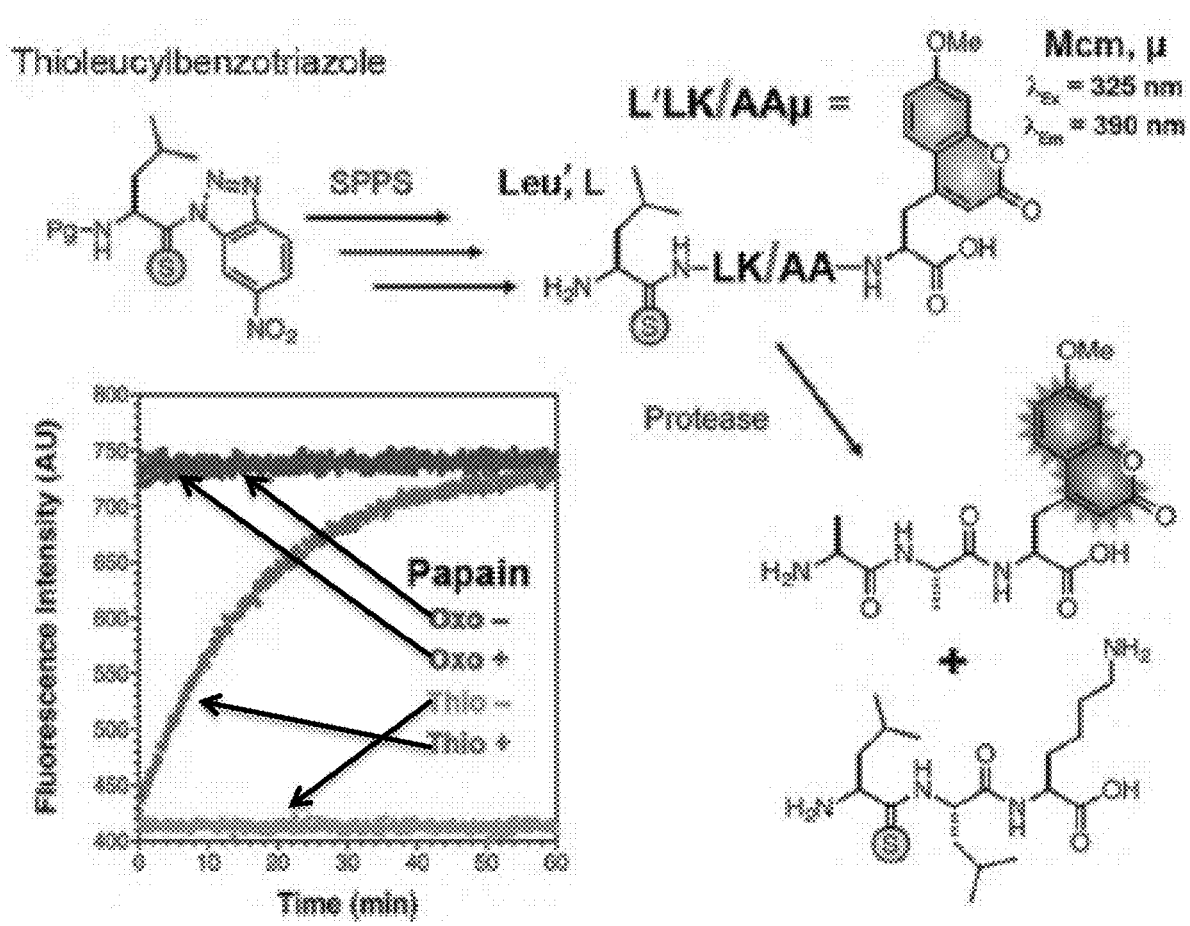
FIG. 2 illustrates thioamide fluorescence quenching applied to proteolysis. Top: Thioamide-containing peptides can be synthesized from benzotriazole precursors. The thioamide bond is denoted with a prime symbol. Bottom left: Cleavage of the substrate L'LKAAµ by papain led to an increase in fluorescence. No change in fluorescence was observed for the oxoamide control peptide (LLKAAµ).

Thioamides can quench fluorophores such as methoxycoumarin (Mcm, μ), and this quenching can be used to monitor protein folding and stability (Goldberg, et al., 2014, J. Am. Chem. Soc. 135:2086-2093). Thioamides may be incorporated into peptides made on solid phase using benzotriazole precursors like the thioleucine precursor shown in FIG. 2. Thioamide-containing peptides of up to 35 residues can be synthesized in reasonable yields (~50% of the corresponding oxoamide peptide), making synthesis of any of the thioamide peptide hormones considered herein straightforward (Goldberg, et al., 2010, J. Am. Chem. Soc. 132: 14718-14720). Thioamides can be used in fluorogenic constructs to monitor proteolysis by relief of a quenching interaction (FIG. 2). Cleavage of the substrate L'LKAAμ by papain is shown in FIG. 2. No change in fluorescence was seen for the oxoamide (LLKAμ), but it was proteolyzed at the same rate as the thiopeptide in an HPLC assay. The thioamide was not disruptive to proteolysis when placed at a site two or three residues away from the scissile bond. Taken together with the studies of thioamide suppression of proteolysis when placed directly at the scissile bond, the data indicate that the effect of the thioamide is very local. Additionally, studies of the stability of thioamides in cell lysates using non-proteolyzable D-amino acid thiopeptides indicated that they are not substantially metabolized by other enzymes.

Example 2: In Vivo GLP-1 Activity Assays

Figure 3:
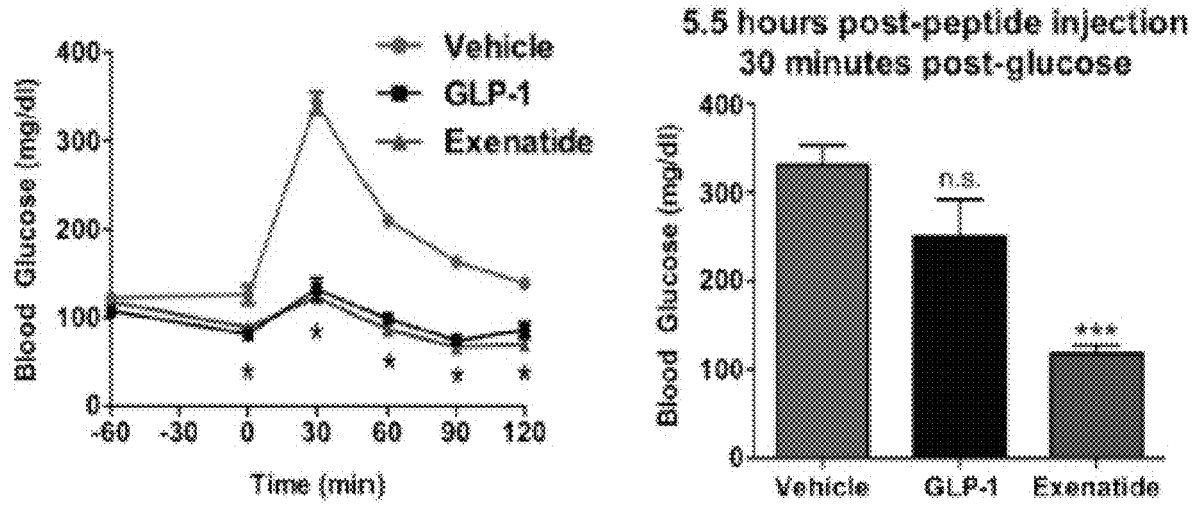
FIG. 3 comprises a set of graphs illustrating glucose tolerance tests (GTTs). Left: Short timecourse GTT to measure the activity of GLP-1 (1 mg/kg) and exendin-4 (1 mg/kg) in vivo. Right: Comparison of the activities of GLP-1 (1 mg/kg) and exendin-4 (1 mg/kg) 5.5 hours after they were injected showed that the more stable exenatide retained activity while GLP-1 did not, due to proteolytic inactivation. Student's t-tests used to determine statistical significance, p-value<0.01, *; p-value<0.0001, ***).

Physiological assays are used to assess the activity of thioamide variants of GLP-1 in regulating glucose control. The activity and half-lives of GLP-1 and exenatide may be determined using glucose tolerance tests (GTTs). In these experiments, mice are injected intraperitoneally (i.p.) with the peptide 60 minutes prior to administration of a glucose challenge (time=0 minutes). Blood glucose levels are measured at −60, 0, 30, 60, 90 and 120 minutes. GLP-1 and exenatide greatly improved glucose tolerance and led to significantly lower blood glucose levels at every time point (FIG. 3, left). This demonstrate that GTTs may be used to measure the in vivo activity of GLP-1 peptides, as well as thioamide GLP-1.

In addition, a GTT may be used to measure changes in the half-life of the bioactive peptides, by increasing the time between the injection of the peptide and the injection of glucose. In an experiment, GLP-1 or exenatide was injected, and then after 5.5 hours glucose was injected. During this waiting period GLP-1 underwent proteolysis and was inactivated, while exenatide retained its activity. In this delayed protocol, measurement of blood glucose levels 30 minutes after glucose injection showed much lower blood glucose levels in exenatide-treated mice (p-value<0.0001), as expected (FIG. 3, right). GLP-1-treated mice experienced only a slight, statistically-insignificant (p-value=0.13) lowering of blood glucose levels compared to vehicle-treated mice. Similar delayed GTT assays are used to determine whether thioamide-modified GLP-1 has increased stability in vivo.

Example 3: Metabolic Stability of Thioamides

Figure 4:
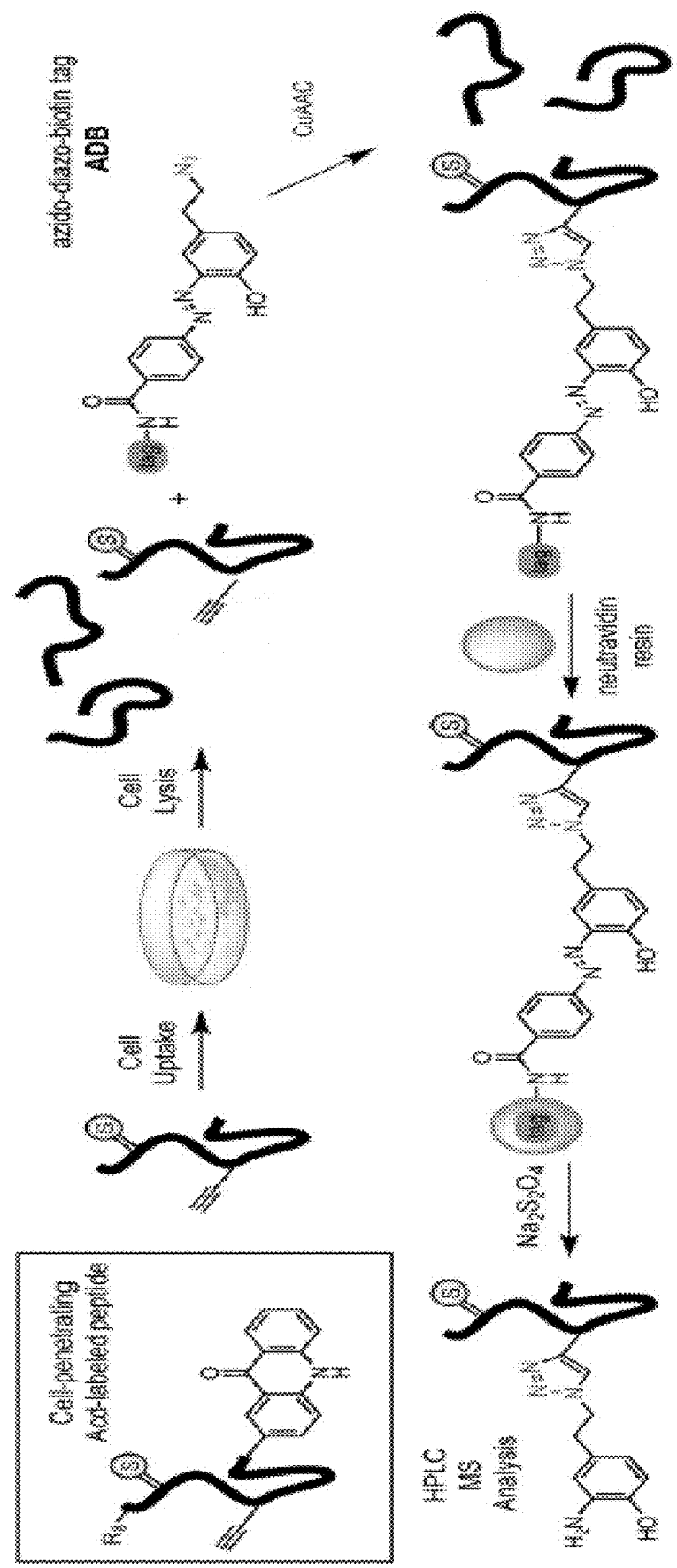
FIG. 4 illustrates thioamide stability assays. Alkyne-modified thiopeptides are incubated with cells or lysates and reacted with a "clickable" azido-diazo-biotin (ADB) pull-down reagent to isolate the products for HPLC MS analysis.

In order to shed light on the pharmaceutical applications of thiopeptides, the stability of peptidyl thioamides toward non-proteolytic degradation is examined. Degradation kinetics of thiopeptides may be tested in PBS buffer, cell lysates, or mouse serum. As a way to develop a stability assay that can be used in cells, tests may be run using a cleavable biotin tag (Yang, et al., 2010, Chem. Biol. 17:1212-1222) to recover the test peptides from the mixture (FIG. 4). The test thiopeptide is labeled with an alkyne group, which reacts selectively with the azido-diazo-biotin (ADB) tag through a copper catalyzed "click" reaction. After the appropriate incubation period, the ADB-tagged samples are purified on neutravadin resin and eluted with $Na_2S_2O_4$. The eluent is then injected onto the HPLC for analysis. The corresponding alkyne-labelled peptide is synthesized for comparison.

Cell-penetrating versions of thioamides may be prepared by appending a poly-Arg sequence. Versions of these peptides are generated with fluorophores such as Acd to monitor cellular uptake and localization (FIG. 4). In addition, changes in fluorescence lifetime may be used in situ to track modifications of the thioamide that would affect quenching of the fluorophore. Changes in lifetime may be monitored in living cells using fluorescence lifetime imaging microscopy (FLIM). These peptides are incubated with MEF and HeLa cells and peptide localization analyzed by microscopy. After appropriate time points, cells are lysed and pull-down assays are performed with ADB to analyze potential thioamide metabolites by HPLC/MS.

Example 4: Proteolysis of GLP-1 and GLP-1 Analogs

As a step in the investigation, GLP-1 itself is studied. To stabilize GLP-1, a thioamide bond can be placed between $Ala_8$ and $Glu_9$, which is the scissile bond of GLP 17-36 ("GLP-1"). In certain embodiments, GLP 19-36 was synthesized on a microwave peptide synthesizer, and then coupled with a thioalanine precursor and His manually. The oxoamide version of GLP-1 was synthesized to serve as a control. Both peptides were synthesized, purified by HPLC, and characterized by MALDI MS.

Example 5: Thio GLP-1 In Vitro Experiments

In certain embodiments, three assays are used to test the stability of thio GLP-1 relative to GLP-1. First, in vitro degradation assays are performed to determine the stability of thio and oxo GLP-1 in the presence of DPP-4. Purified peptides are incubated with DPP-4 in assay buffer for various time periods. The reaction is quenched and the products are analyzed by HPLC to determine the amount of intact peptide. MALDI MS is used to determine the identities of HPLC peaks.

The degradation data indicate that the half-life of thio GLP-1 is greater than 24 hours under conditions where the half-life of GLP-1 is 21 minutes. As demonstrated in FIG. 5, single atom substitution in GLP-1 conferred a roughly 100-fold increase in stability. In addition to HPLC and MS assays, the hydrolysis process can also be monitored by time-resolved UV spectroscopy. Intact thiopeptides exhibit characteristic UV absorption spectra with $\lambda_{max}$ at 267 nm, while the $\lambda_{max}$ of hydrolyzed product thioacid is at 251 nm (this peak disappears when the thioacid further decomposes to the carboxylic acid and $H_2S$). Therefore, the change in absorbance of the reaction at 267 nm or 251 nm may reflect the loss of substrate. These assays may be performed using the Tecan Infinite® M1000 plate reader. The ability to monitor formation of the thioacid cleavage product in real time aims in understanding the mechanism of the proteolysis reaction. In certain embodiments, this information helps understand how thioamide modification may be applied generally to stabilize peptides.

Cleavage of the thioamide bond may be monitored by time-resolved fluorescence spectroscopy. The thioalanine residue can quench the intrinsic fluorescence of $Trp_{31}$ and $Tyr_{19}$ in thio GLP-1. Cleavage of this bond may relieve quenching by PET in a manner similar to the designed fluorogenic probes in the data in FIG. 2. In this case, the thioamide is placed at the scissile bond. Comparison of the fluorescence and absorbance experiments further improves the understanding of thioamide cleavage.

To further describe the interaction between DPP-4 and thio GLP-1, kinetic assays are performed to determine whether thio GLP-1 acts as a competitive inhibitor of DPP-4. Various concentrations of thio GLP-1 are mixed with the same concentration of H-Ala-Pro-pNA, a commercial chromogenic substrate of DPP-4. After addition of catalytic amounts of DPP-4, the reaction may be monitored using the M1000 plate reader. By plotting the relationship between $V_0$ and the concentration of thio GLP-1 in a Lineweaver-Burk analysis, the mechanism of thio GLP-1 inhibition may be determined. Preliminary data indicate that thio GLP-1 acts as an inhibitor, and has the unique attribute of simultaneously acting as both a stabilized GLP-1R agonist and a DPP-4 inhibitor.

Figure 5:
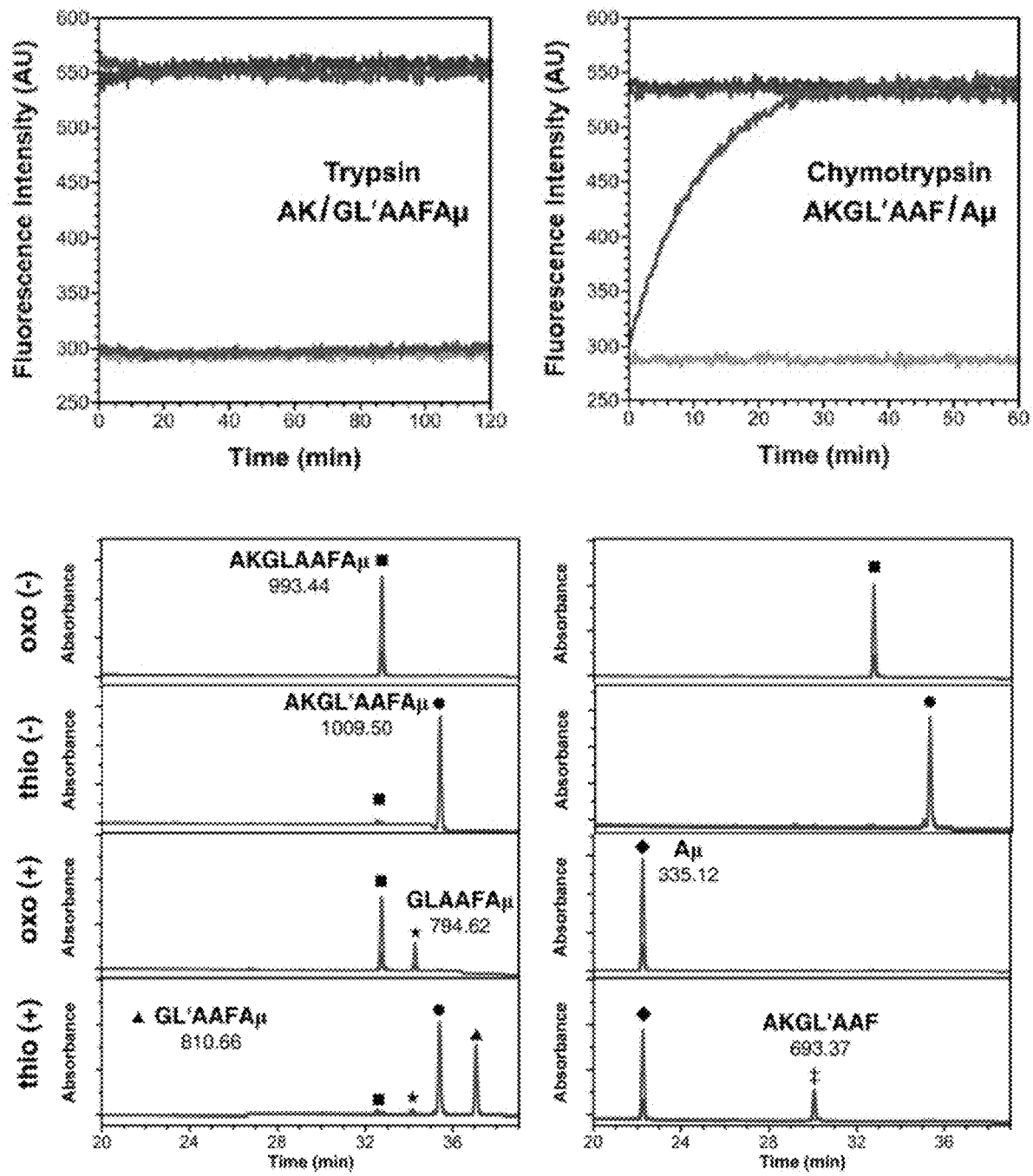
FIG. 5 comprises a set of graphs illustrating the kinetics of hydrolysis of a thioamide-incorporating peptide using trypsin or chymotrypsin (top panel) and HPLC analysis of hydrolysis of peptides and corresponding thioamide-incorporating peptides using trypsin (left) or chymotrypsin (right) (bottom panel).
Figure 6:
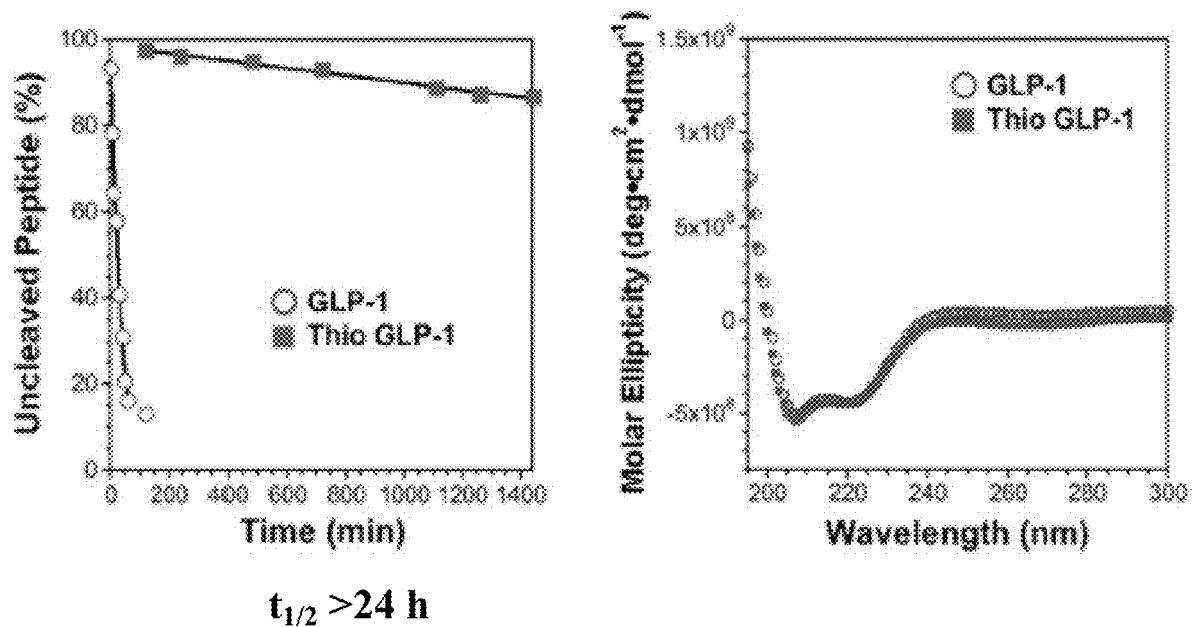
FIG. 6 comprises a set of graphs illustrating thio GLP-1 data. Left graph: Comparison of thio GLP-1 and GLP-1 cleavage by DPP-4. Right: Circular dichroism (CD) spectra of 40 μM GLP-1 and thio GLP-1 in buffer with 30% trifluoroethanol. Thioamide substitution at the GLP-1 scissile bond suppressed proteolysis without disrupting structure (CD) or activity (in vivo).
Figure 7:
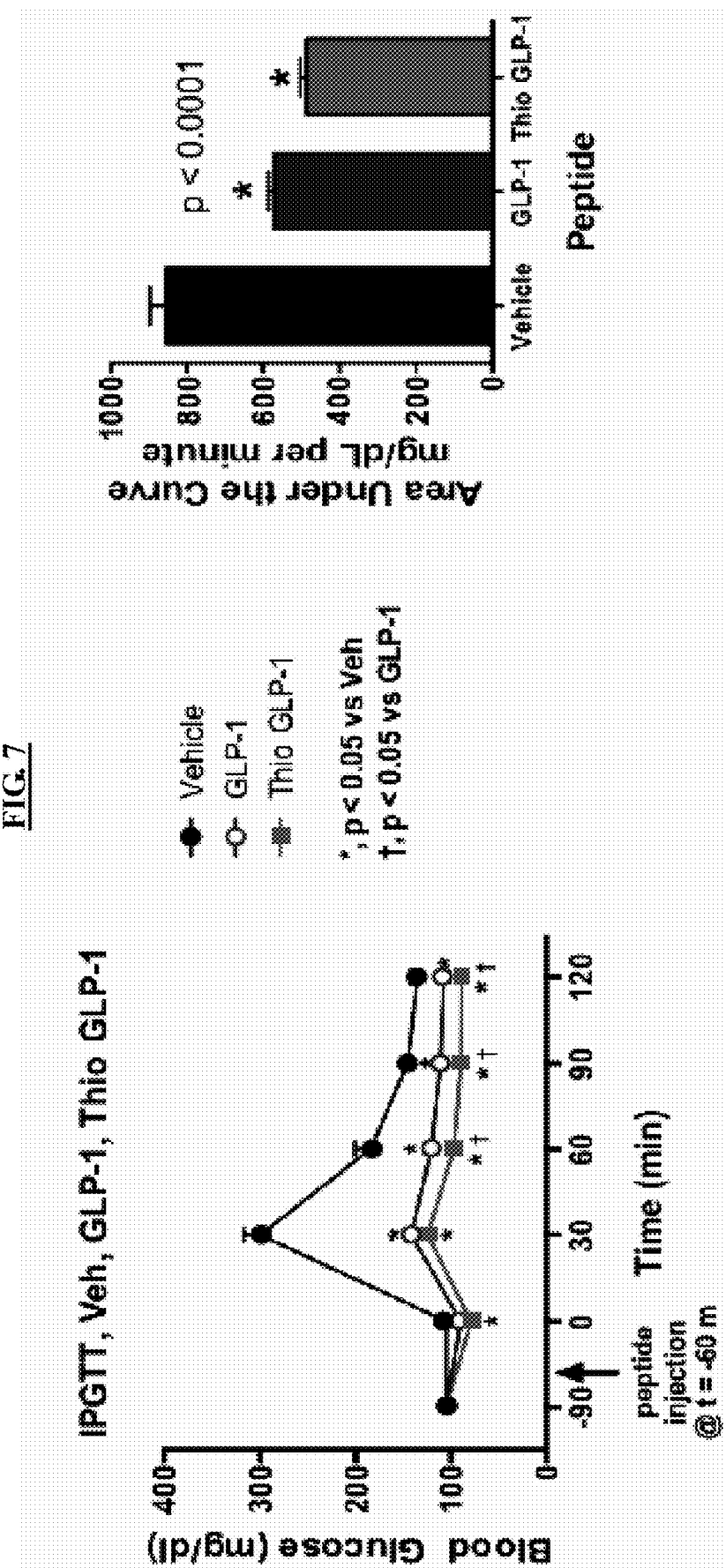
FIG. 7 comprises a set of graphs illustrating experimental results obtained with thioamide-modified GLP-1 ("thio GLP-1") as compared with non-modified GLP-1 ("GLP-1"). The experimental results indicate that thioamide substituted GLP-1 is active in mice. Intra-peritoneal Glucose Tolerance Test (IPGTT) was used to measure activity of GLP-1 (1 mg/kg) and thio GLP-1 (1 mg/kg) in vivo (Student's t-tests used to determine statistical significance).
Figure 8:
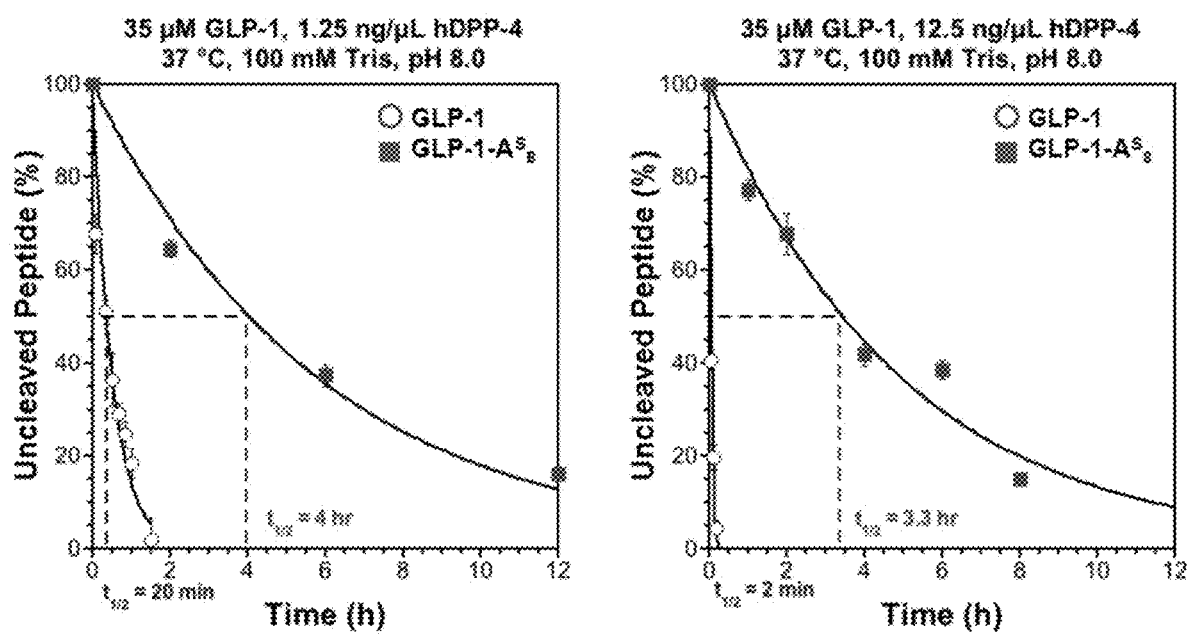
FIG. 8 comprises a set of graphs illustrating the finding that degradation of GLP-1-$A^s_8$ is mitigated compared to that of GLP-1 in presence of DPP-4. GLP-1-$A^s_8$ appeared not to bind to DPP-4, and did not inhibit cleavage of Gly-Pro-pNA substrate at 100 μM.

In certain embodiments, thioamide modification could possibly affect the structure or activity of GLP-1. Circular dichroism (CD) spectroscopy can be used to examine the secondary structure of thio and oxo GLP-1 in the far UV region. As illustrated in FIG. 5, right, the thioamide at $Ala_8$ is not disruptive to GLP-1 folding as the CD signatures are nearly identical, with the notable exception that a small band attributable to the thioamide can be seen at 270 nm in the thio GLP-1 spectrum. The affinity and agonist activity of thio and oxo GLP-1 at the human GLP-1R are determined separately to understand the impact of thioamide modification at $Ala_8$. These two properties are often uncoupled, as in a partial agonist or competitive inhibitor. Affinity is measured using competition assays with fluorophore-labeled GLP-1. Activity is measured using cAMP Hunter eXpress GPCR assay kits (DiscoveRx). Both assays may be performed using the M1000 plate reader.

Example 6: Thio GLP-1 Cellular Experiments

The insulin secretion activity of thio GLP-1 is measured directly using a GSIS assay (Tinoco, et al., 2011, Biochemistry 50:2213-2222). Insulin release in primary mouse islets is examined using the batch release method. GLP-1 or thio GLP-1 is added at 100 nM final concentration to buffer containing basal (1.67 mM) or stimulatory (16.7 mM) glucose concentrations. Islets are incubated for one hour in the assay buffer at 37° C. The supernatant is then collected for insulin measurement using an ELISA, calibrated with a standard curve. In certain embodiments, these assays indicate whether (1) thio GLP-1 affects GSIS, and (2) how this activity compares to GLP-1.

Example 7: Thio GLP-1 In Vivo Experiments

Bioactivity of the thioamide-modified peptides of the invention is evaluated in mice. In a non-limiting example, thio GLP-1 is tested in mice to determine whether it can reduce blood glucose levels after a GTT. GTTs are performed using 12-20 week-old mice, C57BL6/J wild type and Diet-Induced Obese (DIO) mice, after a 14-hour overnight fast. DIO mice are diabetic mouse models that mimic human diabetes associated with weight gain, and experiments with these animals test the ability of thio GLP-1 to improve glucose tolerance in the context of a disease model. Mice (N=6-8 per group) are then injected i.p. with thio GLP-1, GLP-1 or exenatide (positive controls), or vehicle (negative control). Blood glucose levels are measured at −60, 0, 15, 30, 60, and 120 minutes relative to glucose injection.

To determine whether thio GLP-1 has a longer in vivo half-life than GLP-1, this experiment may be repeated with the modification wherein a 5-6 hour delay is inserted between the injection time and the start of the GTT. These animals are sacrificed at the end of the experiment, and serum levels of thio GLP-1 or GLP-1 are measured by LC-MS (Kim, et al., 2012, Proc. Natl. Acad. Sci. USA 109:8523-8527).

Example 8: Thioamide Modification in GLP-1 Analogs

Studies are performed to determine whether thioamide modification can act synergistically with other modifications to stabilize GLP-1. Thio Lira, thio M1, and thio M3 are prepared as well as their oxamide counterparts (Table 1 and FIG. 1). For these syntheses, in certain embodiments, new thioamide precursors such as the Fmoc-benzotriazole version of a may be prepared. The same battery of in vitro tests described for example in Examples 4-6 may be applied to these thiopeptides to determine which peptides to take forward to tests in animals.

Example 9: Additional Signaling Peptides

In addition to GLP-1, several other peptide hormones, including GIP, OXM and BNP, play important roles in diabetes or heart health. Thioamide versions of these peptides are synthesized and then evaluated using the in vitro stability, folding, and activity assays described elsewhere herein. To synthesize these peptides, new thioamide precursors such as Fmoc-thio-Ser(tBu)-benzotriazole and Fmoc-thio-Pro-benzotriazole may be generated. Thiopeptides are tested in the DPP-4 degradation assay to determine whether the stabilization of thioamide modification could be broadly applied. Thio GIP may also be tested in GSIS assays to determine whether it can retain its biological function. GLP-1R and GIP or GCG receptor assays are performed to test the function of thio GIP and thio OXM. Thio BNP activation of natriuretic peptide receptor A may be performed using ELISA kits. Thiopeptides may be further performed in vivo assays.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of stabilizing a bioactive peptide against protease hydrolysis, the method comprising replacing the amide bond formed between the first and second amino acid residues from the N-terminus of the bioactive peptide with a thioamide bond, wherein the protease comprises at least one selected from the group consisting of DPP-4 and carboxypeptidase.

2. The method of claim 1, wherein the bioactive peptide comprises at least one selected from the group consisting of GIP, OCM, GLP-1, NPY, GHRH, ENT, and BNP.

3. The method of claim 1, wherein the thioamide-modified peptide has equivalent biological activity or longer in vivo half-life to the bioactive peptide.

* * * * *